(12) United States Patent
Harada et al.

(10) Patent No.: US 7,664,297 B2
(45) Date of Patent: Feb. 16, 2010

(54) THREE-DIMENSIONAL JOINT STRUCTURE MEASURING METHOD

(75) Inventors: Yoshifumi Harada, Tokyo (JP); Yoshiaki Azuma, Tokyo (JP); Norihiro Yamada, Tokyo (JP); Tsutomu Maeda, Tokyo (JP)

(73) Assignee: Teijin Limited, Osaka (JP)

( * ) Notice: Subject to any disclaimer, the term of this patent is extended or adjusted under 35 U.S.C. 154(b) by 453 days.

(21) Appl. No.: 10/475,694

(22) PCT Filed: Apr. 26, 2002

(86) PCT No.: PCT/JP02/04256

§ 371 (c)(1),
(2), (4) Date: Oct. 24, 2003

(87) PCT Pub. No.: WO02/087444

PCT Pub. Date: Nov. 7, 2002

(65) Prior Publication Data

US 2004/0136583 A1 Jul. 15, 2004

(30) Foreign Application Priority Data

Apr. 26, 2001 (JP) .............................. 2001-129220

(51) Int. Cl.
*G06K 9/00* (2006.01)
*A61B 1/32* (2006.01)

(52) U.S. Cl. ...................... 382/128; 382/132; 600/407; 600/410; 600/427

(58) Field of Classification Search ......... 382/128–131, 382/199, 257, 154, 288; 600/407, 410, 427; 128/922
See application file for complete search history.

(56) References Cited

U.S. PATENT DOCUMENTS 5,247,934 A * 9/1993 Wehrli et al. ................. 600/410
5,835,619 A * 11/1998 Morimoto et al. ............ 382/132
6,021,213 A * 2/2000 Helterbrand et al. ......... 382/128

(Continued)

FOREIGN PATENT DOCUMENTS

| JP | 58-46945 A1 | 3/1983 |
| JP | 06-36047 A1 | 2/1994 |
| JP | 9-322883 A1 | 12/1997 |
| JP | 10-277033 A1 | 10/1998 |

(Continued)

OTHER PUBLICATIONS

Usami, Hiroshi et al., "Gaku Kansetsu Kouchi Ni yoru Kotsukansetsugeki no 3 Jigen Keisokuho no Kento," The Journal of Japanese Society of Stomatognathic Function, vol. 6, No. 1, (1999).

(Continued)

*Primary Examiner*—Vikkram Bali
*Assistant Examiner*—Andrae S Allison
(74) *Attorney, Agent, or Firm*—Rader, Fishman & Grauer, PLLC

(57) ABSTRACT

A method enabling a destroyed part of a joint or joint cartilage to be extracted accurately and at a high speed with a good repeatability and enabling quantitative and simple 3D analysis of the joint and the destroyed part, that is, a method of 3D image processing comprising filling in a medullary cavity region, comprised of a hollow region inside a joint, of a digitalized image of a cross-section of the examined joint using the Expansion and Shrinkage method, performing 3D labeling by a 3D image obtained by stacking digitalized images of cross-sections of the examined joint generated at a step of extracting a contour of the cross-sectional image of the joint or digitalized images of cross-sections of the examined joint not pre-processed, and defining the joint image to be evaluated.

16 Claims, 29 Drawing Sheets

U.S. PATENT DOCUMENTS

| | | | |
|---|---|---|---|
| 6,442,287 B1 * | 8/2002 | Jiang et al. | 382/128 |
| 6,449,502 B1 * | 9/2002 | Ohkubo | 600/407 |
| 6,785,409 B1 * | 8/2004 | Suri | 382/128 |
| 6,799,066 B2 * | 9/2004 | Steines et al. | 600/407 |
| 6,839,457 B1 | 1/2005 | Azuma et al. | |
| 7,133,543 B2 * | 11/2006 | Verwoerd et al. | 382/128 |
| 7,239,908 B1 * | 7/2007 | Alexander et al. | 600/427 |
| 2002/0177770 A1 * | 11/2002 | Lang et al. | 600/410 |
| 2003/0112921 A1 * | 6/2003 | Lang et al. | 378/54 |

FOREIGN PATENT DOCUMENTS

| | | |
|---|---|---|
| JP | 11-112877 | 4/1999 |
| JP | 11-296700 A1 | 10/1999 |
| JP | 2000-126178 A1 | 5/2000 |
| JP | 2000-139870 A1 | 5/2000 |
| JP | 2000-180377 A1 | 6/2000 |
| WO | WO-00/74567 A1 | 12/2000 |

OTHER PUBLICATIONS

Japanese Office Action (corresponding Japanese Application No. 2002-584799) mailed Dec. 20, 2005.

Yao et al. "Tetrahedral Mesh Modeling of Density Data for Anatomical Atlases and Intensity-Based Registration," Medical Image Computing and Computer-Assisted Intervention—MICCAI 2000 Lecture Notes in Computer Science; LNCS, Springer-Verlag, BE, The Johns Hopkins University, Baltimore, MD, vol. 1935, pp. 531-540 (2000).

Browne et al. "Radiographic Image Analysis in the Study of Bone Morphology," Clinical Physics and Physiological Measurement, Institute of Physics Publishing, Bristol, Great Britain, vol. 8, No. 2, pp. 105-121 (May 1987).

Supplementary European Search Report, for European Application No. 02720630.9, mailed Dec. 28, 2007 (3 pages).

* cited by examiner

X0=(i, j, k)         X8=(i−1, j−1, k)
X1=(i, j, k−1)       X9=(i+1, j−1, k)
X2=(i, j−1, k)       X10=(i−1, j−1, k−1)
X3=(i−1, j, k)       X11=(i+1, j−1, k−1)
X4=(i, j−1, k−1)     X12=(i−1, j+1, k−1)
X5=(i−1, j, k−1)     X13=(i+1, j+1, k−1)
X6=(i+1, j, k−1)
X7=(i, j+1, k−1)

→ 91
→ 94
→ 93
→ 92

→ 101
→ 103
→ 102

STEP 1: INPUT IMAGE

STEP 2: EXPANSION PROCESSING (n EXPANSIONS)

STEP 3: SHRINKAGE PROCESSING (n SHRINKAGES)

STEP 4; DIFFERENTIAL IMAGE (STEP 3-STEP 1)

STEP 1: INPUT IMAGE

STEP 2: EXTRACT BOUNDARY PIXEL

STEP 3: FIT FOLLOWING TWO SPHERES ON BOUNDARY PIXEL IN FOCUSED OBJECT

STEP 4: RESULTS OF FILLING RECESSED STRUCTURE

FIG. 14

FIG. 15

| PARAMETER 1 | JOINT VOLUME |
|---|---|
| PARAMETER 2 | JOINT SURFACE AREA |
| PARAMETER 3 | JOINT BS/BV |
| PARAMETER 4 | JOINT SURFACE IRREGULARITY |
| PARAMETER 5 | DESTROYED PART VOLUME |
| PARAMETER 6 | DESTROYED PART SURFACE AREA |
| PARAMETER 7 | DESTROYED PART INSIDE SURFACE AREA |
| PARAMETER 8 | NUMBER OF DESTROYED PARTS |
| PARAMETER 9 | DESTROYED PART BS/BV |
| PARAMETER 10 | DESTROYED PART VOLUME RATIO |
| PARAMETER 11 | DESTROYED PART INSIDE SURFACE AREA RATIO |
| PARAMETER 12 | DESTROYED PART MEAN VOLUME |
| PARAMETER 13 | DESTROYED PART MEAN SURFACE AREA |

| PARAMETER 1 | Joint Space Volume |
|---|---|
| PARAMETER 2 | Joint Space Minimum Distance |

FIG. 23

```
                          START
                            │
STEP 1:  LIST VOXEL COORDINATES OF FEMUR SIDE WHERE FEMUR JOINT PART REGION (1) AND
         MEDULLARY CAVITY REGION (FEMUR SIDE) (3) HAVE CONTACT WITH JS REGION (5)
         (LIST 1).

STEP 2:  LIST VOXEL COORDINATES OF TIBIA SIDE WHERE TIBIA JOINT PART REGION (2) AND
         MEDULLARY CAVITY REGION (TIBIA SIDE) (4) HAVE CONTACT WITH JS REGION (5)
         (LIST 2).

STEP 3:  FIND DISTANCE DATA FROM FEMUR SIDE VOXEL COORDINATE LIST (LIST 1) TO TIBIA
         SIDE VOXEL COORDINATE LIST (LIST 2) AND MAKE SHORTEST DISTANCE JSMD.

END
```

```
 0  0  0  0  0  0  0  0  0  0  0  0  0  0
 0  1  1  1  1  1  1  1  1  1  1  1  1  0
 0  1  3  3  1  1  1  1  3  3  1  1  1  0
 0  1  3  3  1  1  1  1  3  3  1  1  1  0
 0  1  3  3  1  1  1  1  3  3  1  1  1  0
 0  1  3  3  1  1  1  1  3  3  1  1  1  0  ──▷ 2 4 1
 0  5  5  5  5  5  5  5  5  5  5  5  5  0
 0  5  5  5  5  5  5  5  5  5  5  5  5  0
 0  5  5  5  5  5  5  5  5  5  5  5  5  0
 0  2  4  4  2  2  2  2  4  4  2  2  2  0  ──▷ 2 4 2
 0  2  4  4  2  2  2  2  4  4  2  2  2  0
 0  2  4  4  2  2  2  2  4  4  2  2  2  0
 0  2  4  4  2  2  2  2  4  4  2  2  2  0
 0  2  2  2  2  2  2  2  2  2  2  2  2  0
 0  0  0  0  0  0  0  0  0  0  0  0  0  0
```

JOINT VOLUME

JOINT SURFACE AREA

JOINT BS/BV

JOINT SURFACE IRREGULARITY

DESTROYED PART VOLUME

DESTROYED PART SURFACE AREA

DESTROYED PART INSIDE SURFACE AREA

NUMBER OF DESTROYED PARTS

DESTROYED PART BS/BV

DESTROYED PART VOLUME RATIO

DESTROYED PART INSIDE SURFACE AREA RATIO

DESTROYED PART MEAN VOLUME

DESTROYED PART MEAN SURFACE AREA

RESULTS OF MEASUREMENT OF SURFACE IRREGULARITY IN CASE OF NO FILLING OF JOINT INTERNAL STRUCTURE

JS REGION OF KNEE JOINT OF NORMAL GUINEA PIG

JS REGION OF KNEE JOINT OF DISEASED GUINEA PIG

THREE-DIMENSIONAL JOINT STRUCTURE MEASURING METHOD

FIELD OF THE INVENTION

The present invention relates to a method for measuring the shape or surface structure of a joint based on a joint tomographic image, more particularly relates to a method of measurement comprising extracting a joint destroyed part (hereinafter referred to as a "destroyed part") from a joint based on a digitalized image of the joint cross-section whereby it is possible to automatically extract a destroyed part from a joint at a high speed with a good repeatability and obtain a three-dimensional (3D) image separated into the joint and the destroyed part able to serve as the basis of nondestructive analysis of the 3D joint structure. Further, the present invention relates to a method enabling measurement of various structural parameters serving as analytical indicators such of the 3D structure etc. of the joint and destroyed part obtained by the above measurement method.

TECHNICAL BACKGROUND

In the past, as the method for the evaluation of a joint destruction in rheumatoid arthritis, osteoarthritis, or other arthritis, the method of reading a transmission X-ray photograph by physicians has been employed. In reading a transmission X-ray photograph, a comparative study is made by scoring by the Larsen method (Larsen A. et al.; *Acta. Radiol. Diag.* 18, 481 (1977), Larsen A. et al.; *J. Rheumatol.* 22, 1974 (1995)), the improved Sharp method (Sharp T J. et al.; *Arthritis Rheum.* 28, 1326 (1985), van der Heijde D M. et al.; *Baillieres Clin. Rheumatol.* 10, 435 (1996)), the Kellgren Lawrence method (Kellgren J H. and Lawrence J S. et al; *Annals. Rheumatic. Diseases* 16, 494 (1957)), etc. The method of evaluation using such scoring, however, suffers from various problems such as the fact that basically it is qualitative evaluation, it is greatly influenced by the degree of skill of the physician, and the repeatability is poor.

Further, for the joint cartilage, which cannot be directly observed with a transmission X-ray photograph, for example, in the Larsen method or the Kellgren Lawrence method, observation is replaced by indirect evaluation of the changes in the space between the joint bones, in particular the distance between the femur and the tibia, as Joint Space Narrowing (JSN).

Transmission X-ray photographs, however, are transmission images from a specific direction of the examined joint and cause remarkable loss of structural information of the joints, which are originally 3D structures, more particularly the joint surface, joint destroyed part, joint space (JS), and other 3D structural information on the volume, surface area, spatial information, etc. Further, the method of directly evaluating the destruction of the joint cartilage using MRI or ultrasonic waves in addition to transmission X-ray photographs is also being utilized, but this is basically 2D evaluation and therefore does not fundamentally solve the problems in evaluation by transmission X-ray photographs.

As explained above, joints are 3D structures. The joint destruction in rheumatoid arthritis, osteoarthritis, or other arthritis also occurs three-dimensionally, so it is also desirable to analyze the joint destruction three-dimensionally. If 3D analysis were possible, the above problems in 2D analysis could be solved even with indirect evaluation by transmission X-ray photographs etc.

Up until now, we have developed a method of analysis of the 3D bone structure and reported on the usefulness of the 3D bone structure of the lumbar vertebra (*Journal of Japan Society of Bone Morphometry*, 9, 97 (1999), *Journal of Japan Society of Bone Morphometry*, 10, 53 (2000)). Further, we have reported that it is possible to conduct 3D structural analysis of joints using this 3D bone structural analysis method and evaluate the characteristics of its 3D structure (*Journal of Japan Society of Bone Metabolism*, 17, 57 (1999)).

These methods, however, end up being affected by the inside structure of the joint bones, more particularly the trabecular structure in the joint bones, so it can be said to be difficult to accurately evaluate the 3D characteristics of the joint surface and joint destroyed part.

As the method of evaluation of a joint destroyed part, the method of directly measuring the shape of the joint cartilage or joint subchondral bone and the method of extracting the destroyed part from the joint cartilage or joint subchondral bone and measuring the shape of the extracted destroyed part may be considered. However, there is no method of evaluation enabling the demands sought after to be satisfied relating to these concepts. In the above-mentioned 3D bone structural analysis method as well, various image processing methods are being used to study in detail the bone structure of the lumbar vertebra (for example, see WO 00/74567), but no image processing method for extracting the destroyed part of a joint has been able to be developed. Therefore, development of a method, able to extract the destroyed part from a joint accurately at a high speed with good repeatability and able to analyze three-dimensionally the joint and destroyed part quantitatively and simply, has been desired.

In the same way, no image processing method for extracting three-dimensionally the space between joint bones has been able to be developed even for the JSN, the alternative indicator of the joint cartilage destruction at the present time. Therefore, development of a method able to extract the JS region from a joint accurately at a high speed with good repeatability and able to analyze three-dimensionally the region quantitatively and simply, has been desired. Solution of this problem is the object of the present invention.

DISCLOSURE OF INVENTION

The above object is achieved by the following invention. That is, the present invention is able to simply and accurately extract only the 3D image of the evaluated joint on a 3D image obtained by stacking digitalized images of cross-sections of the examined joint by using a 3D image processing means. Further, the present invention is characterized by processing for filling in a joint bone medullary cavity in a joint tomographic image for extracting the morphological characteristics of the joint surface. When reconstructing a joint three-dimensionally based on the digitalized image of the examined joint tomographic image obtained by this processing and analyzing the reconstructed 3D structure, it is possible to analyze the surface structure of the joint without being affected by the inside structure of the joint, which could not be obtained with conventional 3D structural analysis, more particularly the trabecular structure inside the joint. Further, the invention is characterized by image processing for extracting a recessed region part of the joint surface, in other words, the destroyed part, from a 3D image of the joint comprised of this part and other parts by applying the method of combining expansion and shrinkage or the method of scanning irregularities with a sphere of any diameter. In this way, the present invention enables 3D evaluation of the surface structure of a joint and destruction of a joint quantitatively and objectively.

Further, the present invention is characterized by image processing comprising using the method of designating two joint bones forming a joint for analysis and combining 3D expansion and shrinkage or the method of scanning irregularities of the surface by a sphere of any diameter so as to extract three-dimensionally the JS region between joint bones, in other words, the joint cartilage. In this way, the present invention enables 3D evaluation of the JS region between joint bones quantitatively and objectively.

Further, as the method of three-dimensionally extracting irregularity of the joint surface, in other words, the destroyed part, it is possible to use an algorithm using expansion and shrinkage and an algorithm of surface scanning by a sphere and thereby provide the optimal analytical technique for the change of the shape, location, etc. of the examined joint, more particularly the hip joint, finger joints, heel, vertebra, etc.

BRIEF DESCRIPTION OF THE DRAWINGS

FIG. 14 is a 3D display of a destroyed part region extracted using the Sphere Scanning method.

FIG. 15 is a parameter list used in measurement of a destroyed part.

FIG. 22 is a parameter list used in the JS region parameters.

FIG. 23 shows the routine for calculating the Joint Space Minimum Distance.

Figure 1:
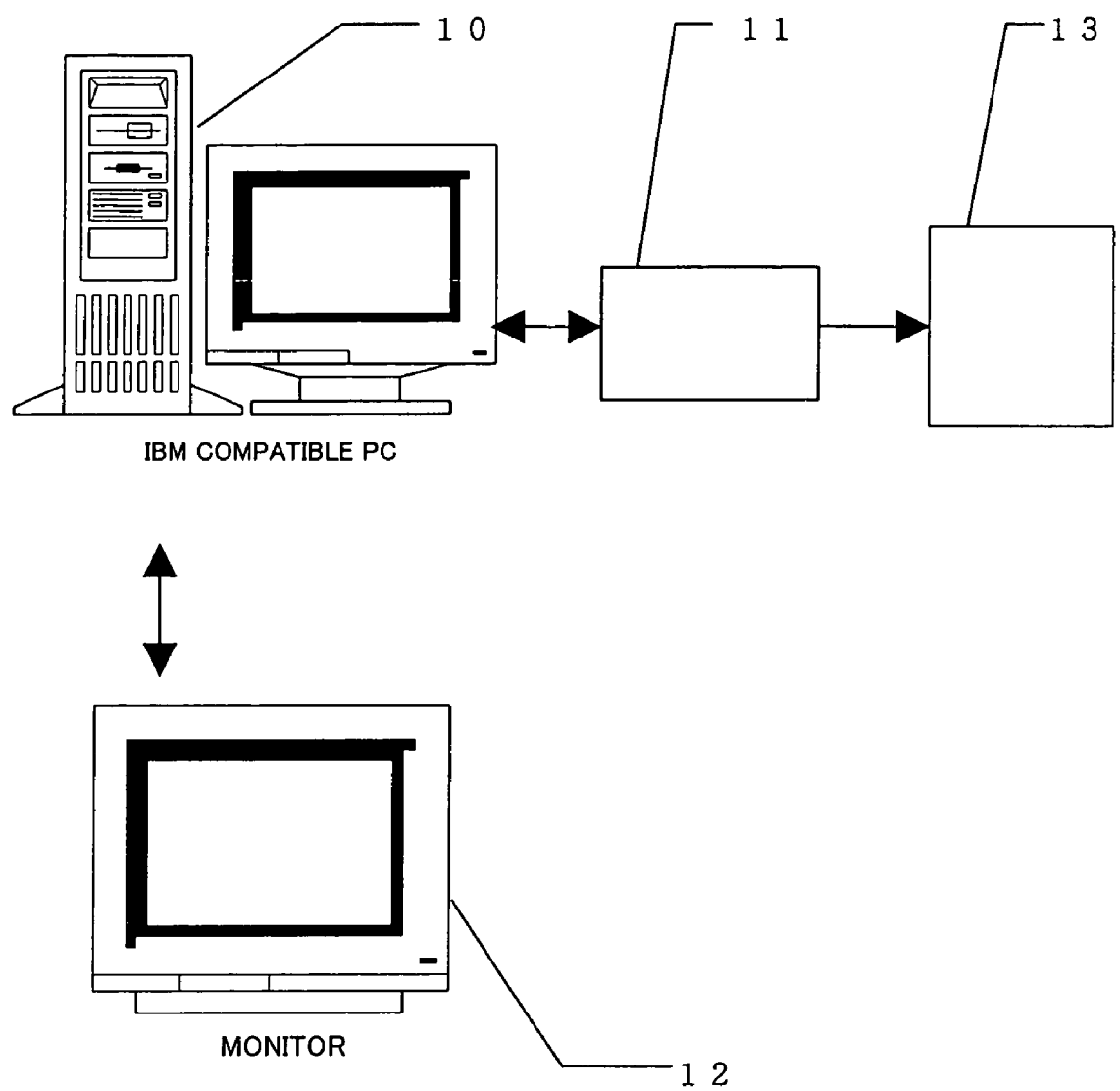
FIG. 1 is an explanatory view of the configuration of an example of the hardware for working the present invention.

The reference numerals in the figures express the following:
10. image processing apparatus
11. personal computer
12. image processing board
13. hard disk
91. tibia
92. femur
93. patella
94. meniscus
101. center of gravity of tibia
102. center of gravity of patella
103. center of gravity of meniscus
131. recessed region extracted by Sphere Scanning method
211. tibia
212. femur
213. JS region and joint destroyed part of tibia and femur extracted by Expansion and Shrinkage method
214. joint destroyed part of femur side
215. joint destroyed part of tibia side
216. JS region
241. voxel list of femur side contacting JS region
242. voxel list of tibia side contacting JS region

DETAILED DESCRIPTION OF THE PREFERRED EMBODIMENTS

Next, examples of application to the knee joint of a rat will be explained in order along with embodiments.

The image of the cross-section of the knee joint of a rat as the examined joint was taken using a microfocus X-ray computer tomographic apparatus (hereinafter referred to as a "µX-ray CT") having a focal dimension and resolution sufficient for measuring the surface structure of the knee joint for the image-taking means in the present example in the same way as the method described in the specification of the above-mentioned WO 00/74567. Note that to obtain an image of the examined bone, it is possible to use another high resolution X-ray apparatus, magnetic resonance imaging apparatus (MRI), or apparatus for generating 2D information of the output image etc. from a film scanner or microscope.

When obtaining an image of the bone using µX-ray CT, visualization of the joint cartilage is difficult under some conditions, but evaluation of the joint subchondral bone is possible. In this case, the object measured is the joint subchondral bone and it is possible to obtain information on its surface shape, the state of irregularities, and destroyed parts of the joint subchondral bone. Further, when using an MRI or other apparatus able to obtain a clear image of the cartilage, the object measured is joint cartilage and it is possible to obtain information on its surface structure, the state of irregularities, and destroyed parts of the cartilage. In the present invention, while the object measured changes according to the image-taking means, it is possible to use the same algorithm to measure the surface structure, state of irregularities, and destroyed parts of the object. In the present invention, regardless of whether the object being measured providing the image of the joint is bone or cartilage, it is possible to measure the joint structure, so the object being examined is denoted as the "joint part" and the extracted destroyed part region as "destroyed part" and a method of structural analysis of general joint structure and joint destroyed part is provided.

The image signal of the examined joint location obtained by the image-taking means is processed by the following image processing apparatus for measurement of the destroyed part. The image processing apparatus 10 of the present example, as shown in FIG. 1, is a personal computer provided with an image processing board 11 dedicated to image processing (in the present example, made by Sharp Semiconductor Co., GPB-K) and a large capacity hard disk 13 for image storage and mounting an external monitor 12 for image display. Further, the apparatus stores the processing routine of the flow chart shown in FIG. 2, processes the image signal of an examined joint obtained by the image-taking means, and automatically extracts the destroyed part region by a predetermined method.

Before the processing, in the same way as the method described in the specification of the above-mentioned WO 00/74567, first an image of the knee joint of the rat being examined is obtained by the μX-ray CT in continuous tomographs at predetermined intervals and loaded into the image processing apparatus. Note that this image should be one giving a spatial resolution of an extent (10 to 30 μm) sufficient for observing the shape of the joint surface. The μX-ray CT image used in the present example is a slice of 512 pixels vertically×512 pixels horizontally×210 in height (axial direction) (maximum 512 slices possible). The dimension per pixel in the cross-section is 37.5 μm, the slice distance 30 μm, and the luminance value CT of each pixel (also called the "concentration value") expressed by $2^8$ gradations. This image is read into the image processing apparatus 10 by input of the original image at step 1 of FIG. 2.

Figure 2:
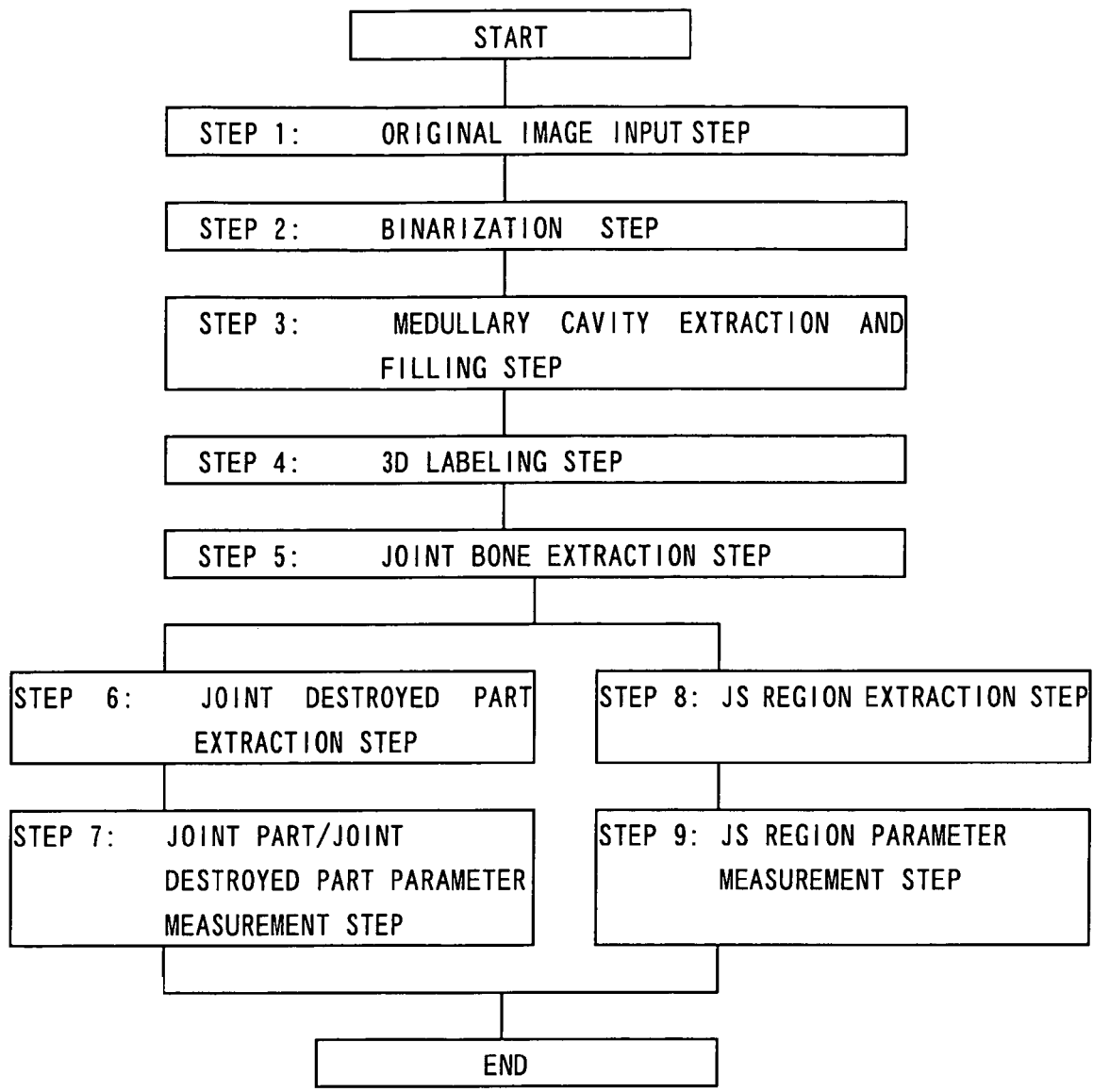
FIG. 2 is an overall flow chart for calculating a joint part, a joint destroyed part, and a JS region.

The digitalization step of step 2 of FIG. 2 is executed to define the joint subchondral bone (hereinafter the "joint part") At that time, the digitalization method uses the following judgement and analysis method.

Figure 3A:
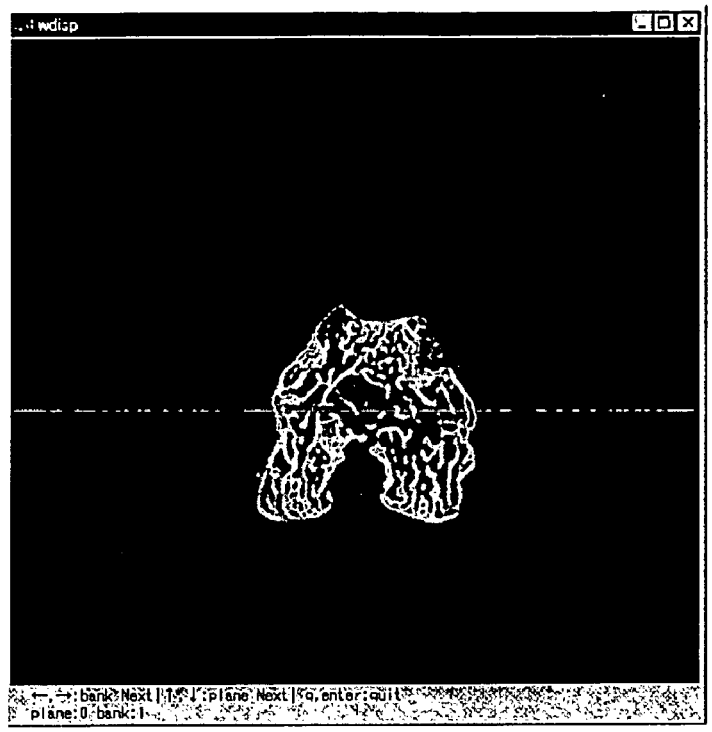
FIG. 3 shows an original image (FIG. 3A) and a digitalized image (FIG. 3B) of the cross-section of a rat femur distal epiphysis.
Figure 3B:
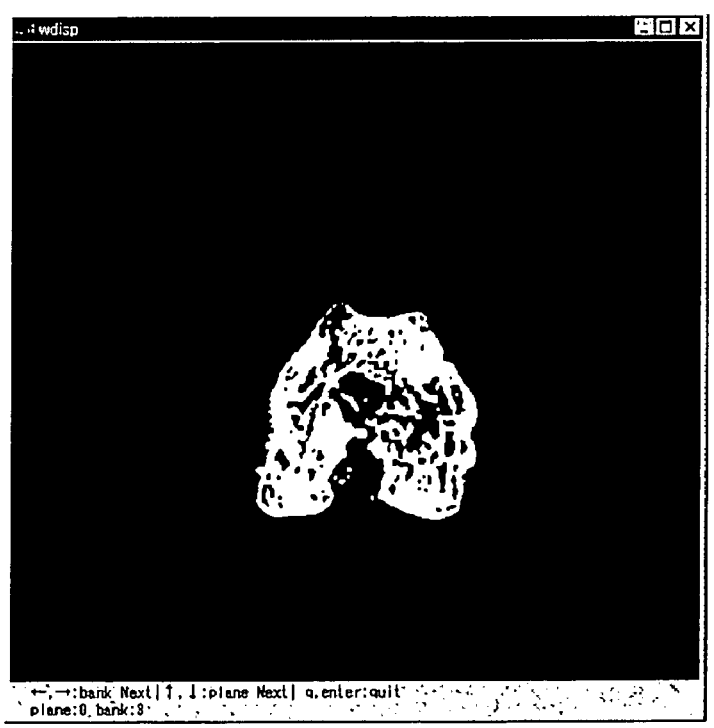

FIG. 3A is the originally taken image of the cross-section of the rat femur distal epiphysis. FIG. 3B is obtained by binarizing (no object "0", object "1") the photographed image for clarifying the joint part and background part. The actual image data is 8-bit data. It is necessary to divide the data into the joint part data and the background data by digitalization.

As the method for the digitalization of the image, use was made of the method of discrimination analysis of the 3D image data. The discrimination analysis method can be used when determining the binarization threshold when the difference in concentration in the group is small and the difference between the groups is large. It is possible to use equation 1 to equation 3 to find the threshold value so that the variance ratio ($F_0$) of equation 1 becomes maximum and thereby detect the joint part:

$$F_0 = \delta B^2 / \delta W^2 \quad \text{Equation 1}$$

where,
$F_0$: variance ratio
$\delta B^2$: Interclass variance
$\delta W^2$: Intraclass variance $$\delta B^2 = \omega_1 \omega_2 (M_1 - M_2)^2 \quad \text{Equation 2}$$

where,
$\omega_1$: Number of pixels of class 1
$\omega_2$: Number of pixels of class 2
$M_1$: Mean luminance value of pixels of class 1
$M_2$: Mean luminance value of pixels of class 2

$$\delta W^2 = \omega_1 \delta_1^2 + \omega_2 \delta_2^2 \quad \text{Equation 3}$$

where,
$\delta_1$: Variance of luminance values of pixels of class 1
$\delta_2$: Variance of luminance values of pixels of class 2

The method for determining the threshold value by the above method is called the "discrimination analysis method". By stacking the joint tomographic image data detected by this discrimination and analysis method in the slice direction, a 3D image (FIG. 4) of the knee joint is obtained.

Next, the step for extracting the medullary cavity of step 3 of FIG. 2 will be explained.

What is actually analyzed in the 3D joint structural analysis is the recessed structure of the bone surface, that is, the joint destroyed part. In this case, the complicated joint inside structure shown in FIG. 3B becomes noise in analysis of the structural characteristics of the joint surface, so the joint internal cavity (hereinafter "medullary cavity") is extracted in advance to prepare a filled image of the joint inside structure, in other words, the sum (OR) image of the joint part and the medullary cavity part. It becomes possible to accurately analyze the structural characteristics of the joint surface by this image processing.

Figure 5A:
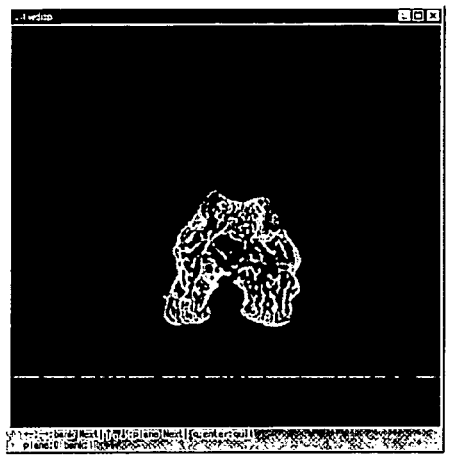
FIG. 5 (FIG. 5A to FIG. 5G) is a group of images showing steps for extracting the medullary cavity from the cross-section of a rat femur distal epiphysis.
Figure 5B:
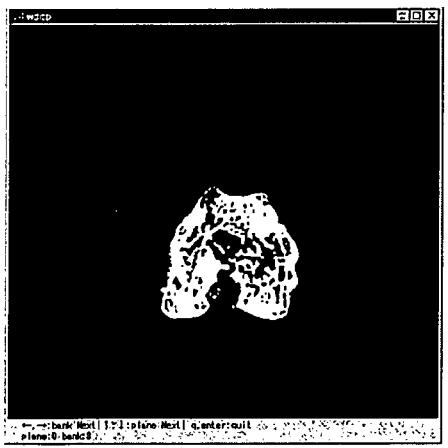
Figure 5C:
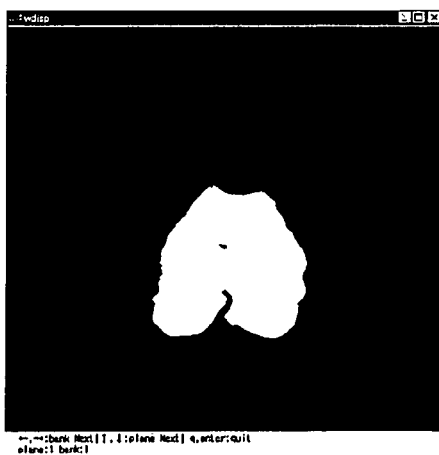
Figure 5D:
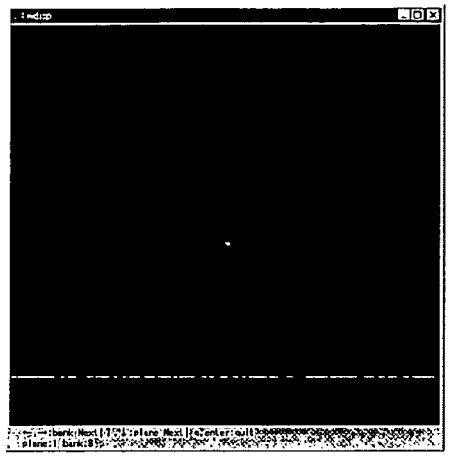
Figure 5E:
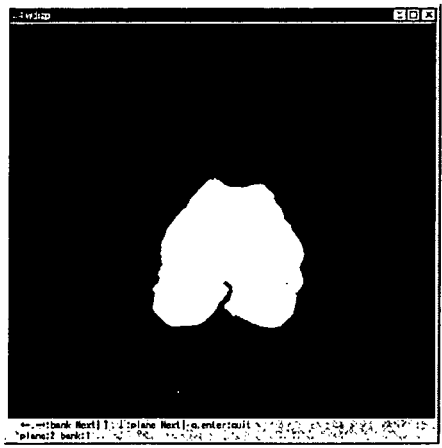
Figure 5F:
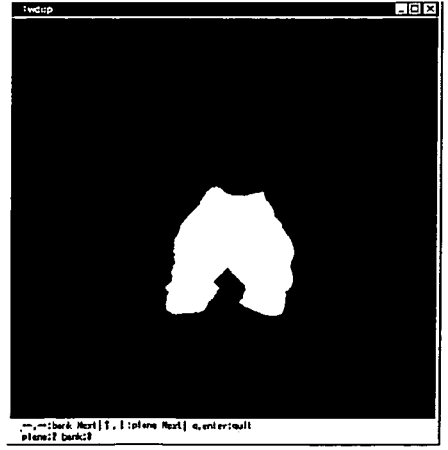

The routine is to perform n number of expansion processings (FIG. 5C) on the joint part image (FIG. 5B) digitalized by the above discrimination analysis method, then detect the hole part image (FIG. 5D) other than the maximum hole part to obtain the sum (OR) image (FIG. 5E) of the hole part image (FIG. 5D) and expansion image (FIG. 5C). Next, it performs n number of image shrinkage processings (FIG. 5F). In the case of the present embodiment, n was made 10 from the interval between the divided parts.

Figure 5G:

Next, by finding the differential image of the digitalized image (FIG. 5B) from the image shrinkage image (FIG. 5F), it is possible to detect the medullary cavity image (FIG. 5G). By stacking the medullary cavity image data detected here in the slice direction and performing m number of expansion processings and m number of shrinkage processings three-dimensionally, a 3D image of the medullary cavity (FIG. 6) is obtained.

Next, the step for 3D labeling of step 4 of FIG. 2 will be explained.

Figure 4:
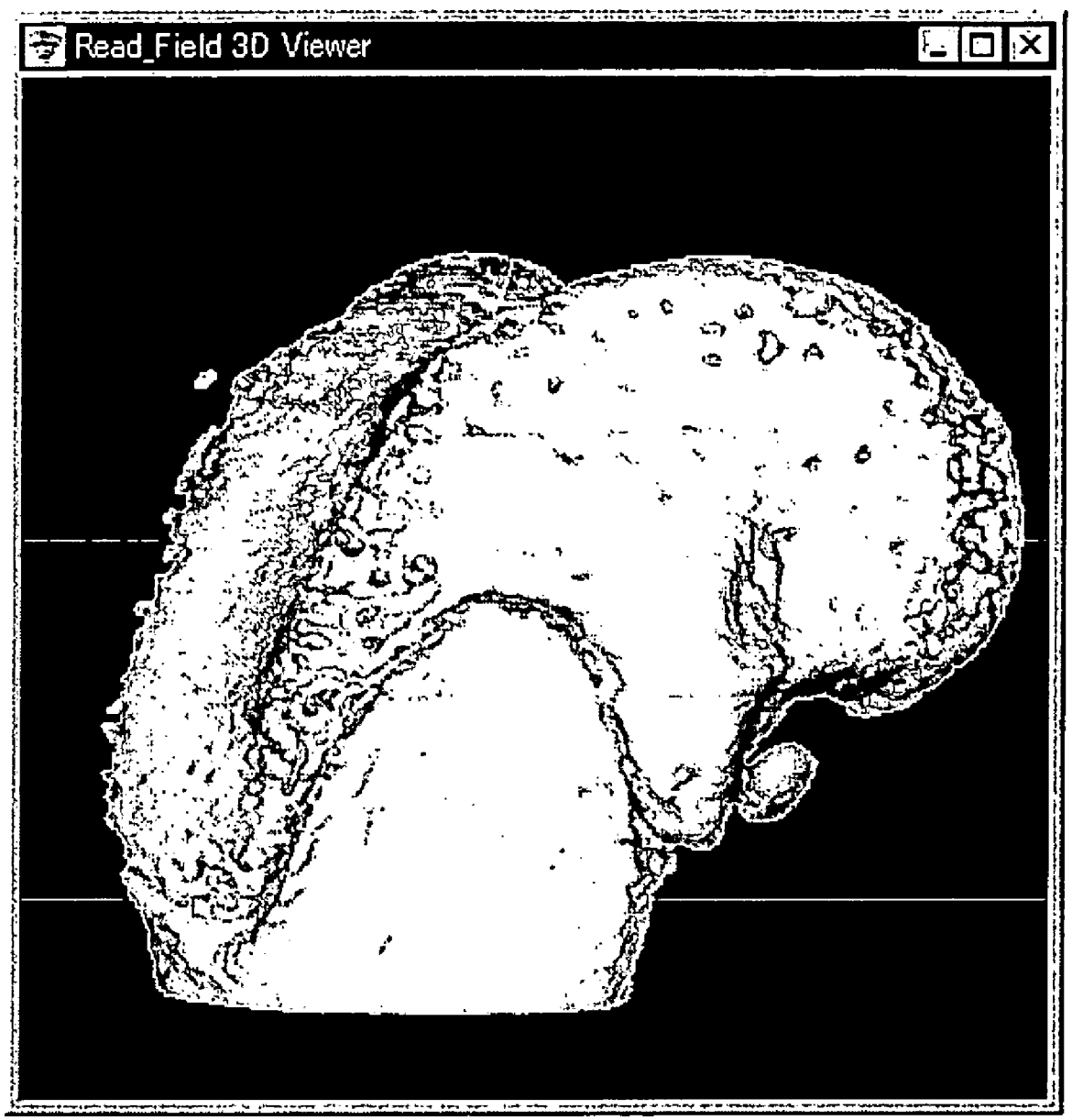
FIG. 4 is a 3D visualized image of subcartilaginous bone of a rat femur distal epiphysis.
Figure 6:
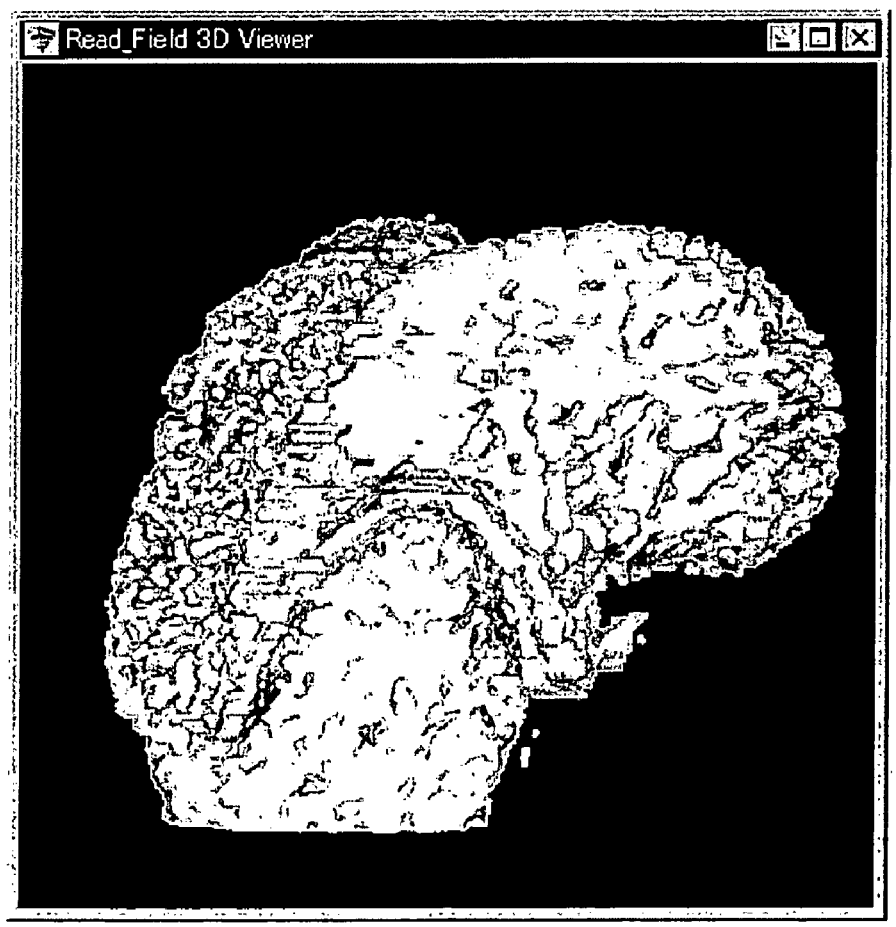
FIG. 6 is a 3D visualized image of the medullary cavity of a rat femur distal epiphysis.

The 3D labeling processing is performed on the 3D image data of the joint part using the filled image of the medullary cavity (sum (OR) image of FIG. 4 and FIG. 6). It is performed as pre-treatment for extracting the analyzed joint part shown in step 5 of FIG. 2. Further, the "labeling" spoken of here judges if the objects are connected, defines the label number for the objects connected three-dimensionally, and counts the number of connections when there are objects between adjoining data designated for the 3D image data.

Figure 7:
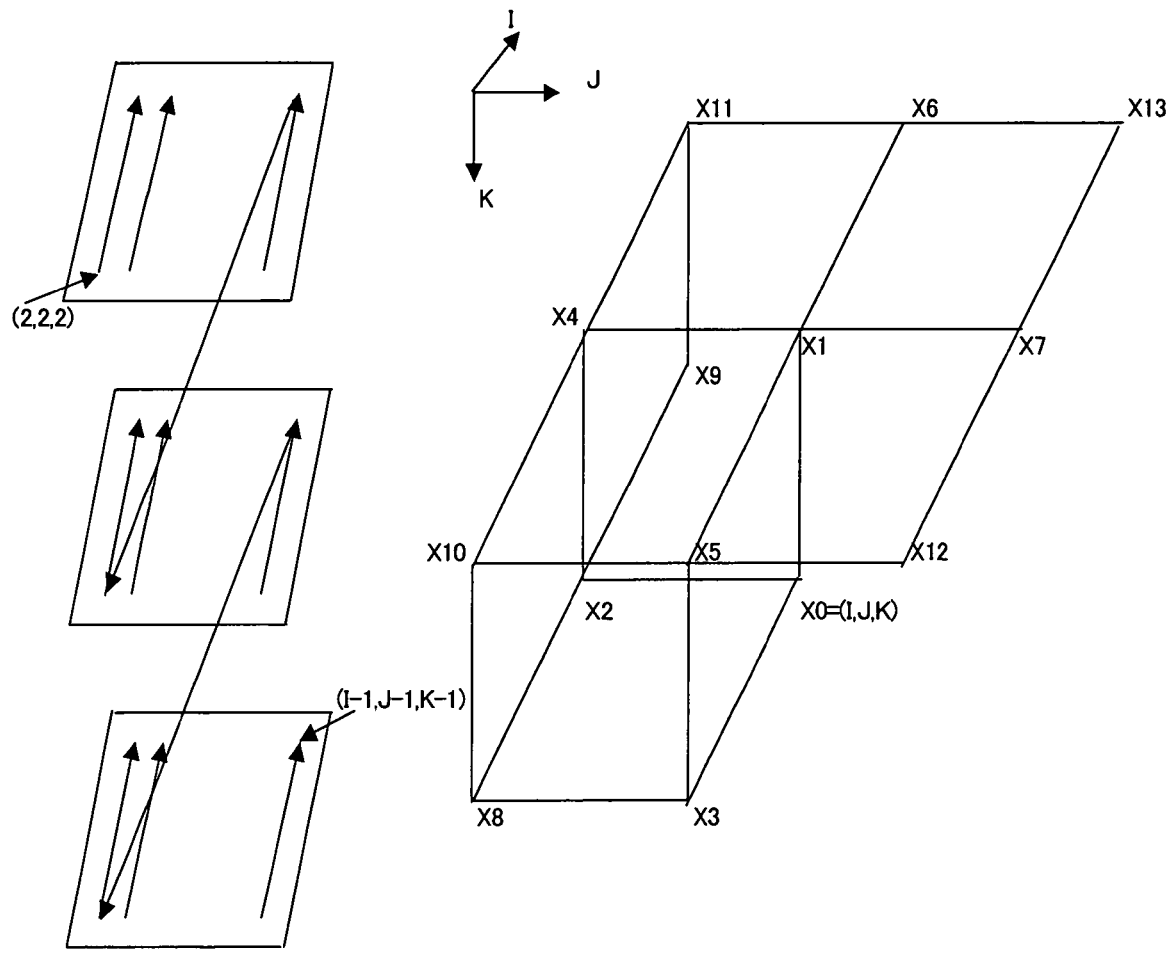
FIG. 7 is an explanatory view of the 3D labeling routine.

The scanning method, as shown at the left of FIG. 7, scans from the element (2,2,2) to the element (i-1, j-1, k-1). At that time, the current element is expressed by x0=(i, j, k) and the nearby scanned elements (X1, X2 . . . , X3) are expressed as shown at the right of FIG. 7. Further, the label (value of image L) of Xp is abbreviated as Lp. When there are close to 26 connections, P=13 is used, while when the connections are near 6, P=3 is used.

Figure 8:
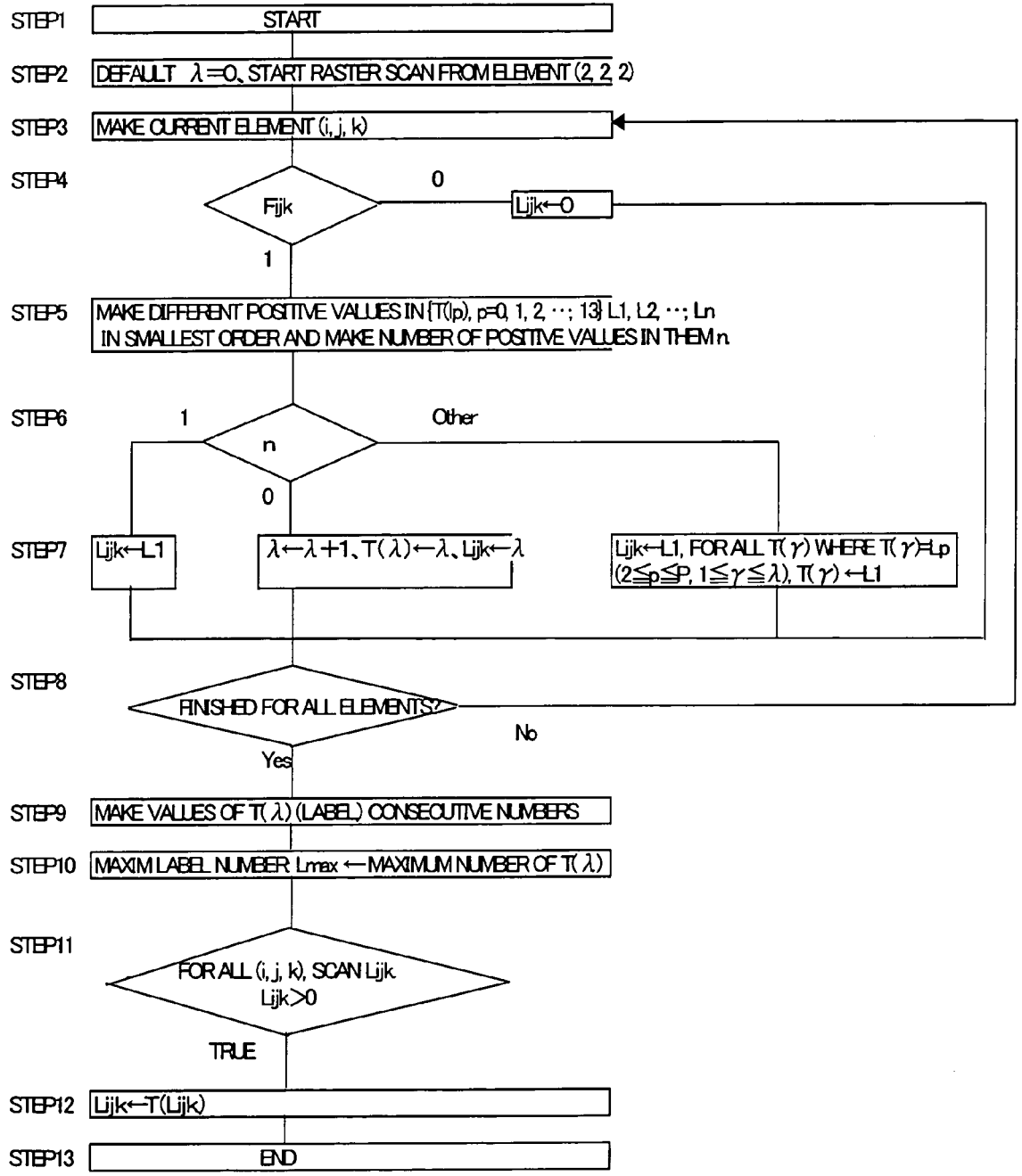
FIG. 8 is a flow chart of the 3D labeling routine.

FIG. 8 shows a flow chart of the algorithm. First, at step 2, the variable λ expressing the connection part (hereinafter referred to as "λ") is initialized to 0. The element for starting the scan is made (2, 2, 2). At step 3, the current element is defined as (i, j, k) and, at step 4, the processing is branched depending on whether the input image (Fijk) is 0 or 1. When 0, there is no object there, so the label image Lijk is made 0 and step 8 is executed. On the other hand, when the input image (Fijk) is 1 at step 4, at step 5, there are made n types of different positive values among {T(Lp):P=0, 1, 2, . . . , 13}. These are made L1, L2, Ln in the order of the smallest value.

Figure 9:
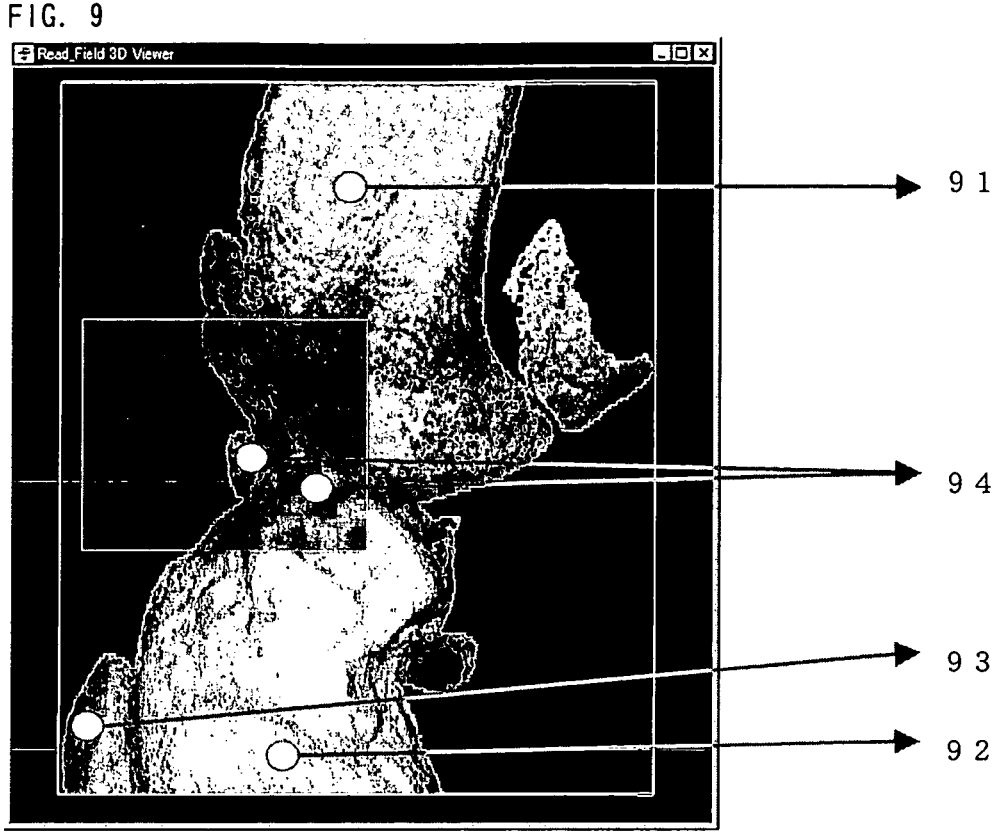
FIG. 9 is a 3D display of joint bones of a rat knee joint.

Further, at step 6, the processing is branched at step 7 corresponding to the value of n. When n=0, the object appears for the first time, so λ←λ+1, the label table T(λ)←λ is inserted, the label table Lijk←λ is inserted, and step 8 is executed. When n=1, there is only one object of the same connection part, so the label table Lijk←λ is entered and step 8 is executed. In other cases, there are a plurality of objects with the same connection parts, so the smallest label number L1 is entered in the label image Lijk, T(γ)=L1 is entered for all T(γ) where T(γ)=Lp(2≦p≦P, 1≦γ≦λ), and step 8 is executed. At step 8, if there are no longer any elements to be scanned remaining, the routine proceeds to step 9, while if there are any remaining, the routine returns to step 3. Step 3 to step 8 are repeated until there are no longer any elements to be scanned left. At step 9, since there are missing numbers in the label table T(λ), the numbers are reallocated to make them consecutive. At step 10, the maximum value of the label numbers stored in the label table T(λ) is detected and that made the maximum label number:Lmax. Next, at step 13, all of the label images are scanned. If larger than 0, at step 12, by entering the consecutively numbered label table T (Lijk) for Lijk, all of the processing is completed. The final label image Lijk stores the 3D labeling data, while the maximum label number is stored in Lmax. The results of labeling near 26 using the actual rat-knee joint part are shown in FIG. 9.

Next, the extraction of the analyzed joint part shown at step 5 of FIG. 2 will be explained. This extraction processing is performed for the purpose of extracting the analyzed object from the joint parts since there are a large number of these in the examined joint region as shown in FIG. 9.

By the 3D labeling processing shown in step 4 of FIG. 2, all of the independent joint parts present in the examined joint region are assigned independent label numbers, so it is possible to designate the 3D structure of any label number, in other words, any joint part as the analyzed joint part.

Further, in the present invention, when making the knee joint part the analyzed object, an algorithm was developed for automatically judging, identifying, and extracting the joint images to be evaluated, that is, the femur, tibia, patella, and meniscus, from the correspondence of the center of gravity positions of the knee joint.

Figure 10:
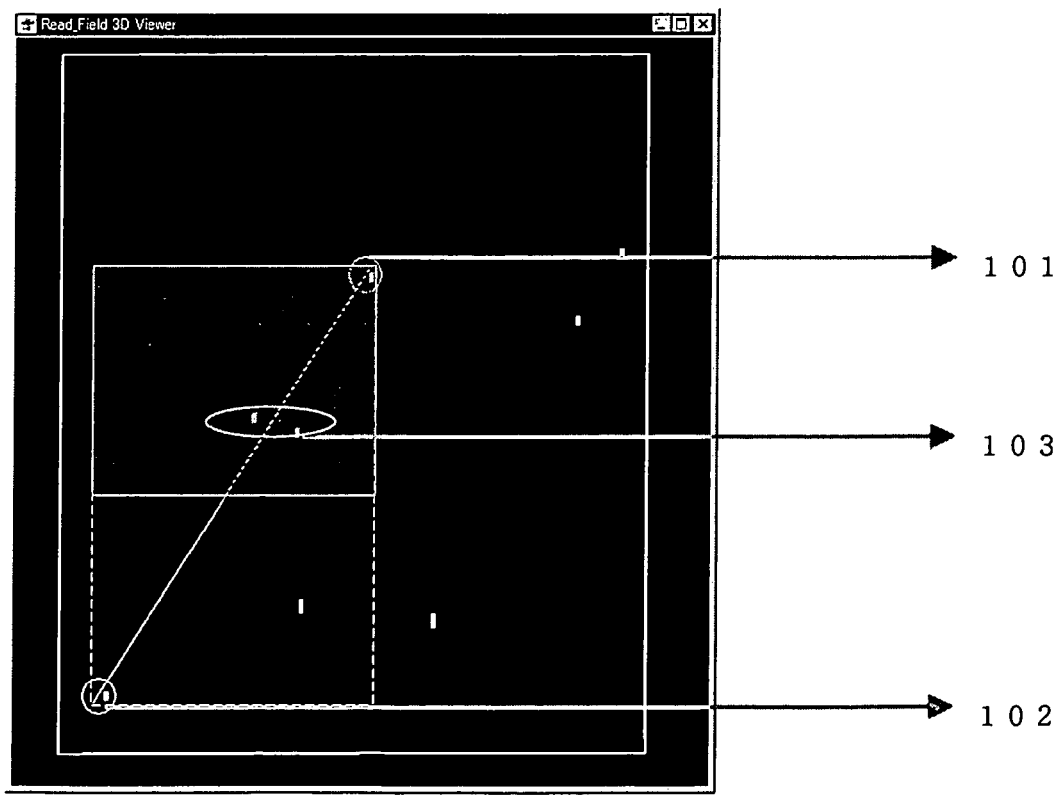
FIG. 10 is a 3D display of center of gravity positions of joint bones at a rat knee joint.
Figure 11A:
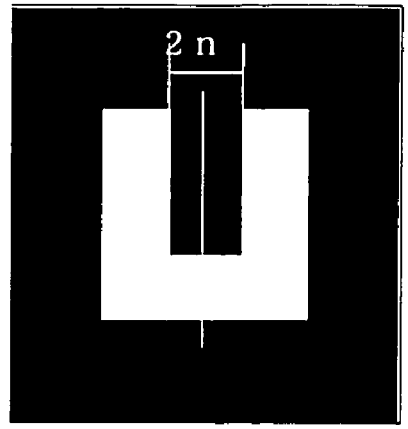
FIG. 11 (FIG. 11A to FIG. 11D) shows the routine of an extraction method of a destroyed part region using the Expansion and Shrinkage method.
Figure 11B:
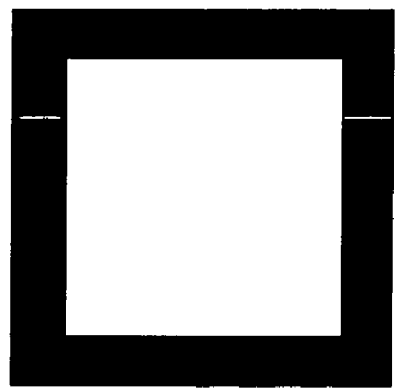
Figure 11C:
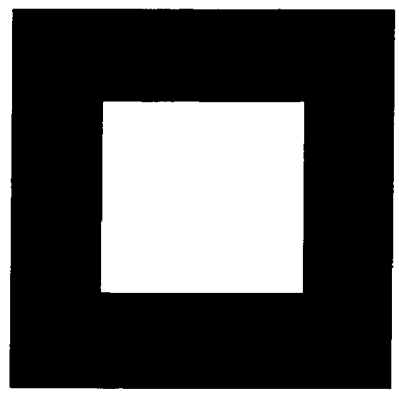
Figure 11D:
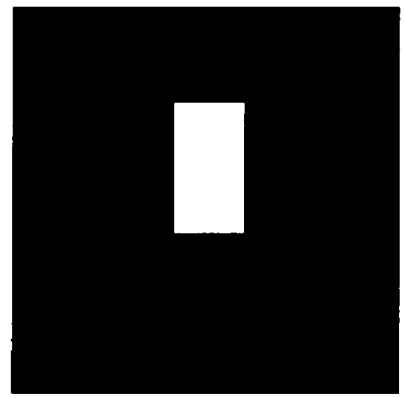

In the present example, the method of extracting the femur, tibia, patella, and meniscus to be analyzed using the rat knee joint (FIG. 9) will be explained. In explaining the method of extraction, the CT tomographic slice image taken is comprised of a group of slice images in the order from the tibia to the femur direction (smaller slice image numbers show tibia side). First, the method of extraction of the tibia part consists of approaching the first of the CT tomograph slice images and extraction using the characteristic of the greatest number of voxels. The number of voxels is defined as the number of voxels of each label image by counting the frequency of each label number at the label image Lijk. The method of extraction of the femur consists of approaching the last of the CT tomograph slice images and extraction using the characteristic of the greatest number of voxels. The method of extraction of the patella consists of similarly approaching the last of the CT tomograph slice images and extraction using the characteristic of the second greatest number of voxels. The method of extraction of the meniscus consists, as shown in FIG. 10, of calculating the center of gravity coordinates of the joint parts being analyzed and defining the group of labels present at the top half (direction of smaller numbers of CT tomographic slice image) of the region defined from the center of gravity coordinates of the patella and center of gravity coordinates of the tibia as the meniscus. By defining the extracted femur as the value 32, the tibia as the value 64, the patella as the value 96, and the meniscus as the value 128, it is possible to analyze the 3D structure shown below for each part being analyzed.

Figure 12:
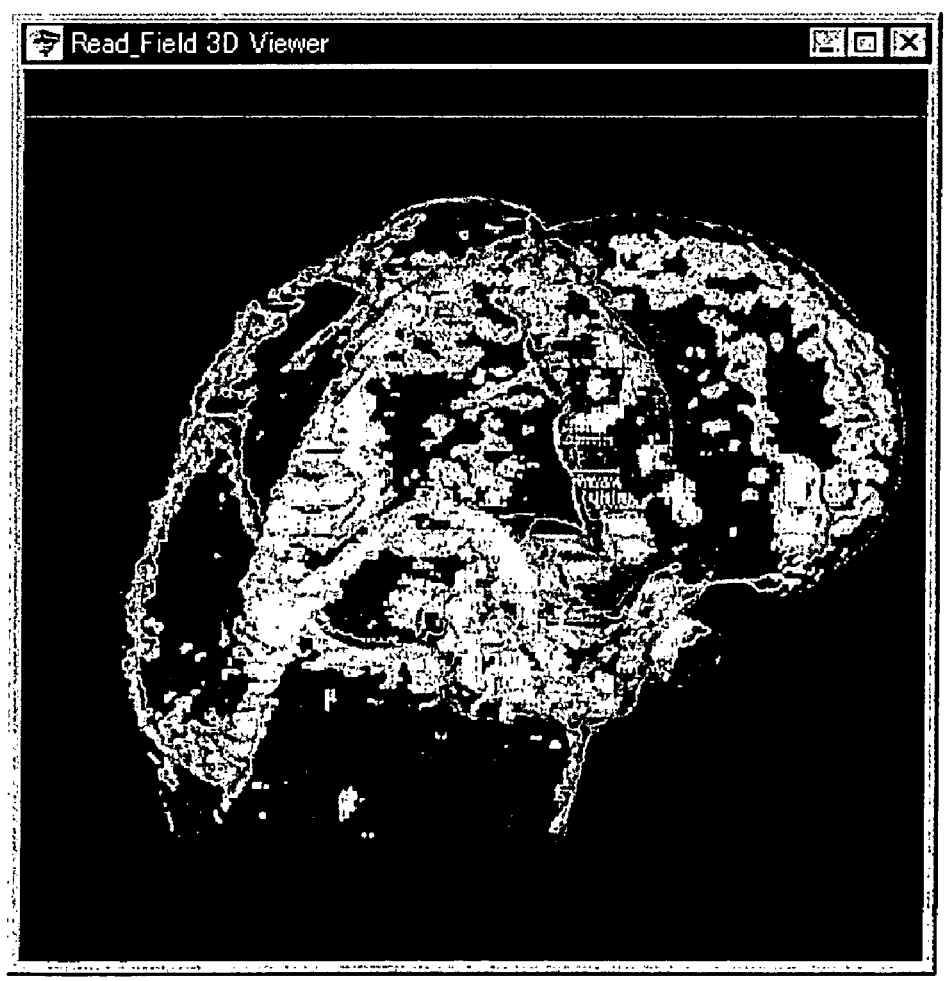
FIG. 12 is a 3D display of a destroyed part region extracted using the Expansion and Shrinkage method.
Figure 13A:
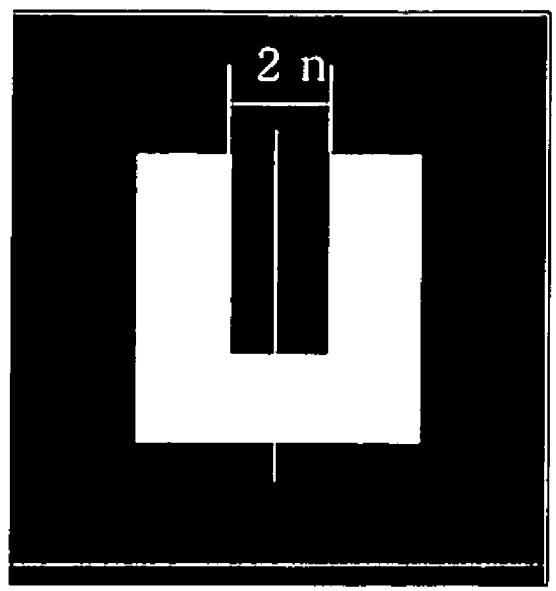
FIG. 13 (FIG. 13A to FIG. 13D) shows the routine of an extraction method of a destroyed part region using the Sphere Scanning method.
Figure 13B:
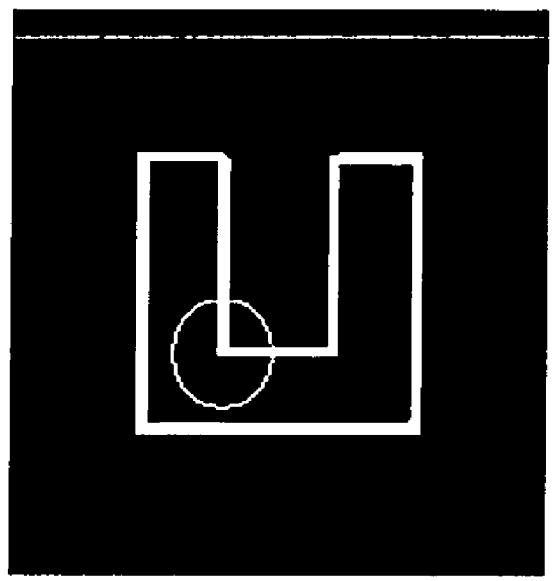
Figure 13C:
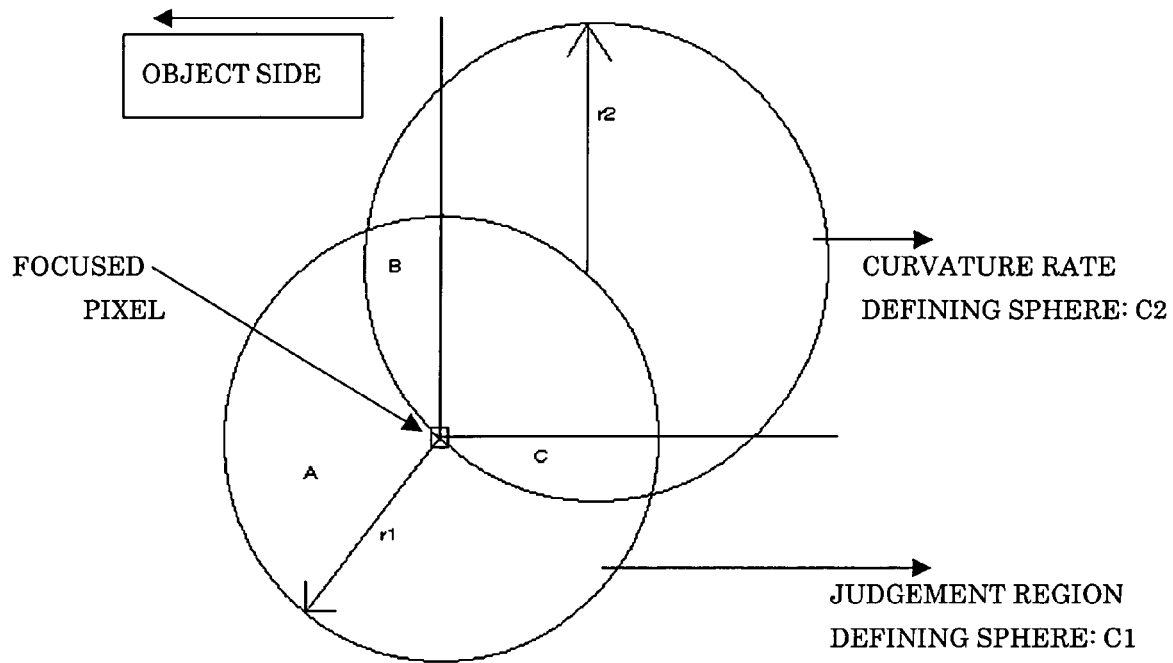
Figure 13D:
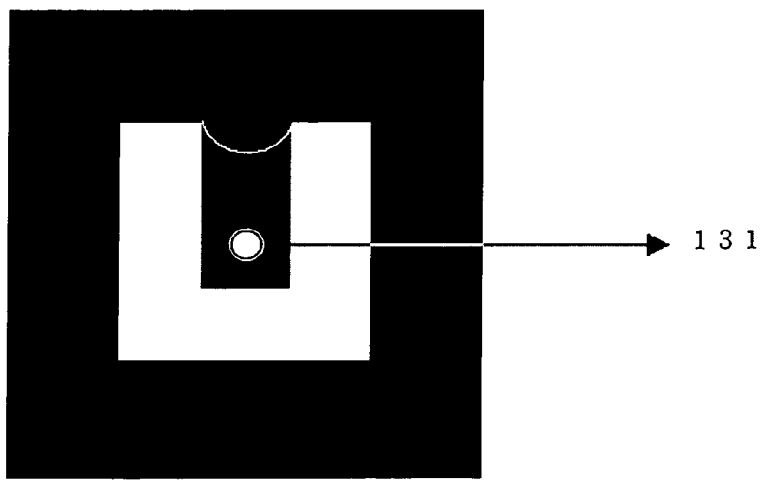

Next, the processing for extraction of the destroyed part shown at step 6 in FIG. 2 will be explained in order of the steps. In the present invention, we developed the method of utilizing expansion and shrinkage for extraction of a recessed region (hereinafter called the "Expansion and Shrinkage method") and the method of successively Scanning spheres at a boundary pixel in question and judging whether to extract the pixel in question from the ratio of overlap of the object and the sphere (hereinafter called the "Sphere Scanning method"). First, the former Expansion and Shrinkage method will be explained. FIG. 11 shows the principle simply in two dimensions. First, at step 1, an input image for explanatory use is prepared. This image is made an object of white (hereinafter "1-pixels") and a background of black (hereinafter "0-pixels"). As a recessed structure, a 2-n pixel block-shaped hole was prepared. The "pixel" is a unit expressing the magnitude of the image. At step 2, the results of expansion of the image n times are shown. In this case, the image boundary also becomes larger, but the 2-n pixel hole is also filled. At step 3, the results of shrinkage of the image n times are shown. The sizee of the image as a whole matches with the input image, but it is learned that the recessed region is filled. At step 4, the input image (step 1) is subtracted from the shrunk image (step 3), whereby it becomes possible to extract the image of only the recessed region. A characteristic of the Expansion and Shrinkage method is the advantage that it is possible to extract a recessed region of two times the number of expansions designated and the time for calculation is comparatively fast. An example of the extraction of the destroyed part of the femur distal epiphysis of a rat having joint destruction is shown in FIG. 12.

Next, the latter method, that is, the Sphere Scanning method, will be explained in the order of steps. FIG. 13 shows briefly the principle of this. First, at step 1, an explanatory use input image is prepared. This image is made an object of white (hereinafter "1-pixels") and a background of black (hereinafter "0-pixels"). As a recessed structure, a 2-n pixel block-shaped hole was prepared. Next, at step 2, a boundary pixel of the object is extracted. The method of extraction of the boundary pixel consists of judging a focused pixel to be a boundary if there is a 0-pixel at a neighboring pixel of a focused 1-pixel. Next, at step 3, a judgement region defining sphere (hereinafter referred to as a "sphere C1") of the radius r1 is fit over the boundary focused pixel and the volume overlapping the object is counted. In the case of this example, the region (A+B+C) corresponds to this. Further, when desiring to fill the recess in a manner giving a certain extent of curvature, a curvature defining sphere of a radius r2 (hereinafter the "sphere C2") is fit so as to cover the sphere C1 at the center and the region (a) where the sphere C1 and sphere C2 do not overlap is made the judged volume. Whether to fill the focused 1-pixels or not is judged by the following equation 4.

Volume of region (A+B+C)>Volume of region (A)   Equation 4

When the region (A+B+C) is larger than the volume of the region (A), the focused boundary pixel, that is, the 1-pixel, is processed to be filled. If performing this processing for the entire image until there are no longer locations to be filled, it is possible to define the filled image (131 in FIG. 13D) of step 4. This Sphere Scanning method is characterized by being able to tolerate gentle irregular structures of the surface of the 3D structure being evaluated and being able to selectively extract sharp changes in the surface structure. An example of extraction of the destroyed part of the femur distal epiphysis of a rat having joint destruction using the Sphere Fitting method by the method of scanning of the left of FIG. 7 is shown in FIG. 14.

Next, the method of calculation of the structural parameters of the destroyed part of step 7 of FIG. 2 will be explained. The items definable as the structural parameters of the destroyed part are shown in FIG. 15.

The handling of the voxel values of the joint part region, medullary cavity region, destroyed part region, and background region as preconditions are defined as follows:
(a) Joint part region→1
(b) Medullary cavity region→2
(c) Destroyed part region→3
(d) Background region→0

Figure 16:
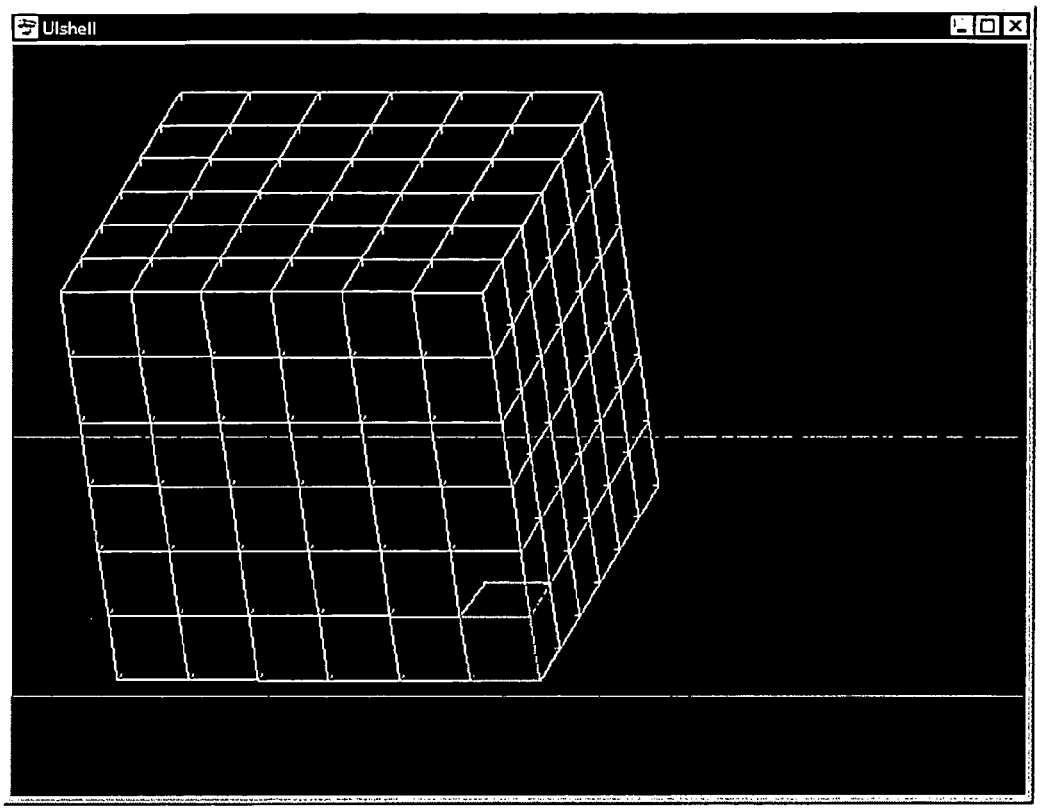
FIG. 16 is a view for explaining the definition of a voxel.
Figure 17:
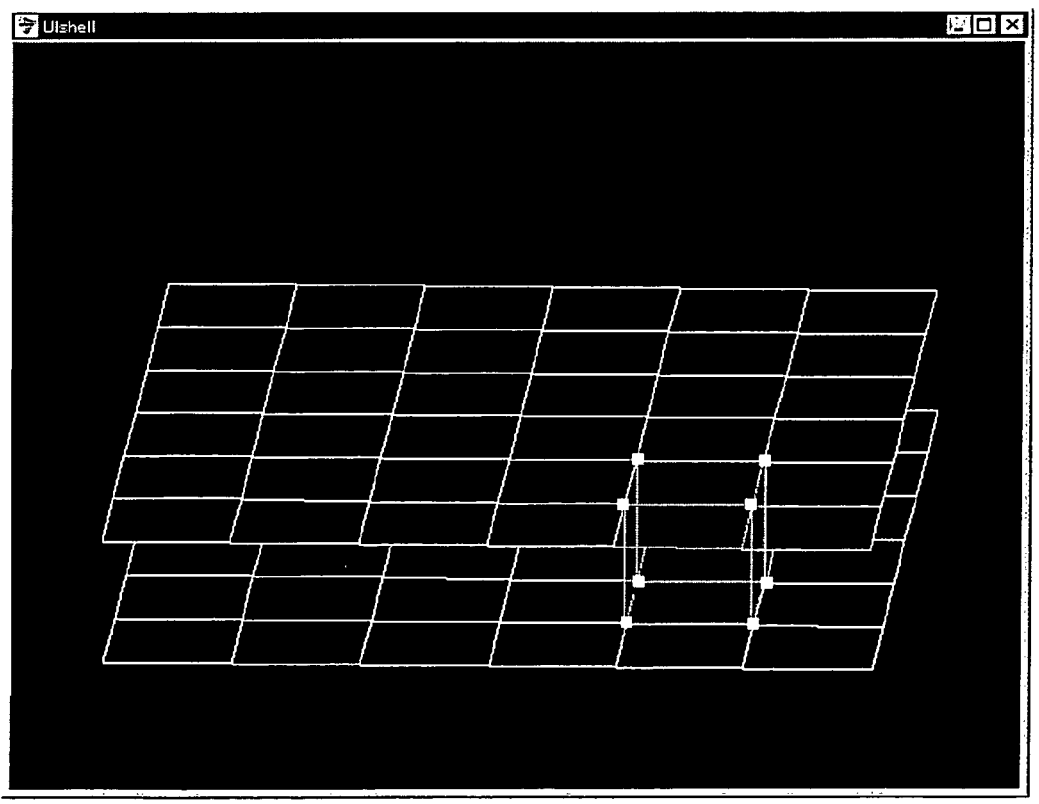
FIG. 17 is a view for explaining the definition of a cube in the advanced Marching Cubes method.

A "voxel" is the smallest cube of FIG. 16. The voxel value is the value defined on the cube. (a) corresponds to the joint part region data digitalized at step 2 of FIG. 2, (b) corresponds to the medullary cavity region extracted at step 3 of FIG. 2, and (c) corresponds to the destroyed part region extracted at step 6 of FIG. 2. The voxel value of the joint part region is defined as "1", the voxel value of the medullary cavity region as "2", the voxel value of the destroyed part region as "3", and the voxel value of the background region as "0".

Figure 18:
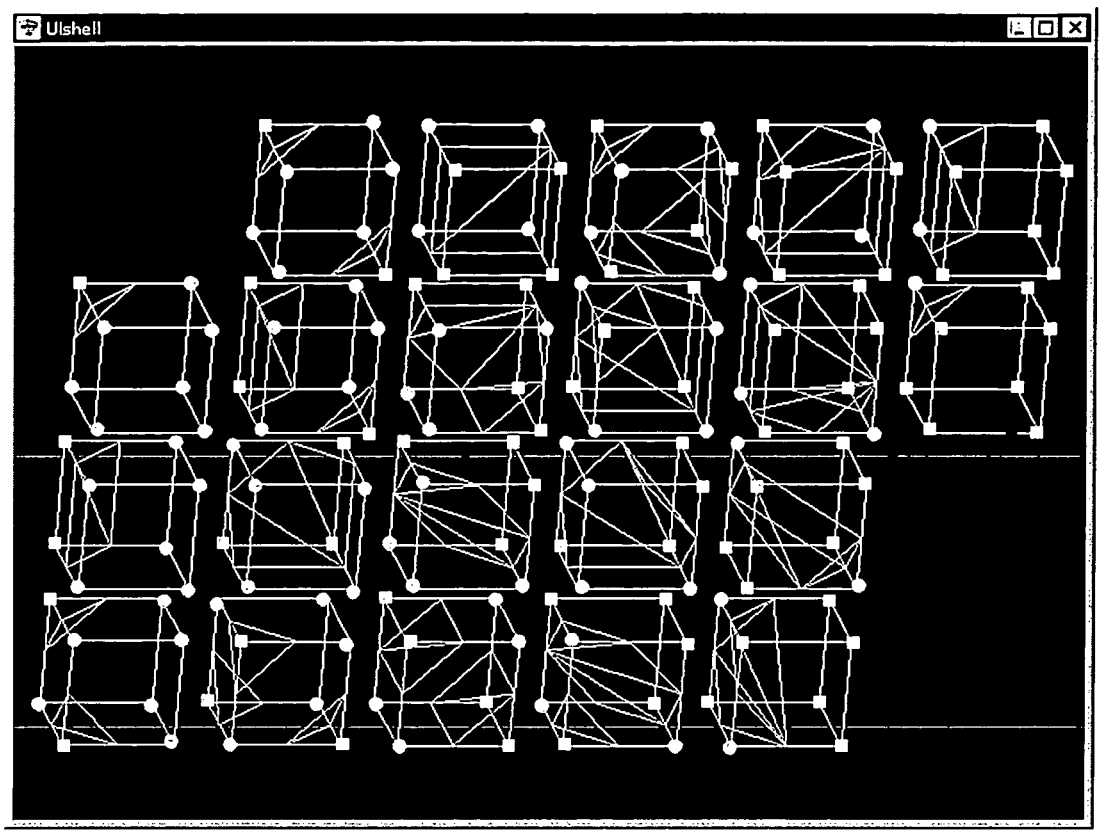
FIG. 18 is a view of a cube pattern and boundaries used in the advanced Marching Cubes method.

First, the joint volume and joint surface area of the parameter 1 and parameter 2 of FIG. 15 will be explained. When measuring the joint volume and joint surface area, the method of defining the boundary surface of the object (Advanced Marching Cubes method: Japanese Patent No. 02798561) is applied and an image processing means defining the image to give continuous triangles at the boundary surface is used. The Advanced Marching Cubes method is the method of defining in advance the boundary surface as shown in FIG. 18 by the 21 patterns of voxel values conceivable from the 2×2×2 patterns of eight cubes (FIG. 12) centered on a voxel and defining the boundary region by pattern matching with the actual model. To define the boundary of the joint, consider a joint part region having a voxel value of 1 and medullary cavity part having a voxel value of 2 as a single object and define a surface at the boundary of data divided at regions other than this (voxel value of 0 or 3). Therefore, by defining cubes sampled from the 2×2×2 voxel region from the joint part data and the boundary surface by pattern matching on the cubes of FIG. 18 and counting the cube data and boundary surface data, it becomes possible to calculate the joint volume and the joint surface area.

Next, the method of finding the parameter 3 of FIG. 15, that is, the joint BS/BV, will be explained. The joint BS/BV is calculated by equation 5:

$$\text{Joint } BS/BV = \text{Joint surface area}/\text{Joint volume} \quad \text{Equation 5}$$

The joint BS/BV expresses the magnitude of the surface area per unit volume and is one indicator of the complexity of the surface structure of the joint part.

Figure 19:
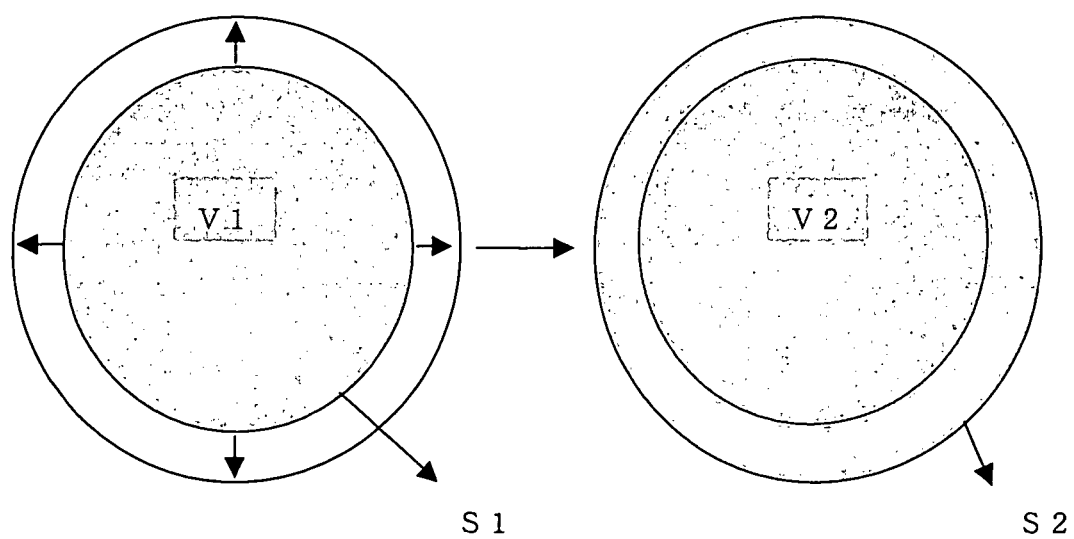
FIG. 19 is a view of the method of calculation of bone surface irregularity.

Next, the method of finding the parameter 4 of FIG. 15, that is, the joint surface irregularity, will be explained. The joint surface irregularity is calculated by equation 6.

$$\text{Joint surface irregularity} = (S2-S1)/(V2-V1) \quad \text{Equation 6}$$

where,
S1: Surface area before 3D image expansion
V1: Volume before 3D image expansion
S2: Surface area after 3D image expansion
V2: Volume after 3D image expansion As shown in FIG. 19, the volume (V1) and surface area (S1) show the volume and surface area before expansion, while the volume (V2) and surface area (S2) show the volume and surface area after image expansion (one voxel is a worth of expansion). The value found from this equation becomes positive at a projecting structural part, while becomes negative at a recessed surface part. Therefore, as an overall structure, the value becomes positive for a structure comprised mostly of projecting structures, while the value becomes negative for a structure comprised mostly of recessed structures. When the numbers of projecting structures and recessed structures are substantially equal, the value becomes close to zero.

Next, the destroyed part volume and destroyed part surface area of the parameter 5 and parameter 6 of FIG. 15 will be explained. In measuring the destroyed part volume and destroyed part surface area, in the same way as the parameter 1 and parameter 2 of FIG. 15, the method of defining the boundary surface of the object (Advanced Marching Cubes method: Japanese Patent No. 02798561) is used and an image processing means defining the image to give continuous triangles at the boundary surface is used to find the destroyed part volume and destroyed part surface area.

Next, the method of finding the parameter 7 of FIG. 15, that is, the destroyed part inside surface area, will be explained. The destroyed part surface area expresses the surface area of the part where the joint region (a) and destroyed region (c) overlap. In this case, by applying the Advanced Marching Cubes method to just the pattern where the joint part region (a) and destroyed part region (c) are present on the cubes, the destroyed part inside surface area is found. The destroyed part inside surface area, in other words, means the surface area of the destroyed part at the joint surface and is an important indicator in judging the extent of the joint destruction.

Next, the method of finding the parameter 8 of FIG. 15, that is, the number of destroyed parts, will be explained. By applying 3D labeling explained at step 4 of FIG. 2 to the destroyed part region (c), the number of the independent entities on the image are found. This number corresponds to the number of the destroyed parts.

Next, the parameter 9 of FIG. 15, that is, the destroyed part BS/BV, is found by equation 7:

$$\text{Destroyed part } BS/BV = BS/BV \quad \text{Equation 7}$$

where,
BS: Surface area of destroyed part
BV: Volume of destroyed part

The destroyed part BS/BV expresses the amount of the surface area per unit volume and is one indicator expressing the complexity of the destroyed part structure.

Next, the method of finding the parameter 10 of FIG. 15, that is, the destroyed part volume ratio, will be explained. The definition of the destroyed part volume ratio is found by calculation of equation 8:

$$\text{Destroyed part volume ratio} = \text{Destroyed part volume}/(\text{joint part volume} + \text{medullary cavity volume} + \text{destroyed part volume}) \quad \text{Equation 8}$$

Next, the method of calculating the parameter 11 of FIG. 15, that is, the destroyed part inside surface area ratio, will be explained. The definition of the destroyed part inside surface area ratio is found by calculation of equation 9:

$$\text{Destroyed part inside surface area ratio} = \text{Destroyed part inside surface area}/\{\text{surface area of (joint part region OR medullary cavity region)}\} \quad \text{Equation 9}$$

Next, the method of calculating the parameter 12 of FIG. 15, that is, the mean volume of destroyed parts, will be explained. The mean volume of destroyed parts expresses the mean volume per destroyed part independent in observation area. Equation 10 shows the method of calculating it;

$$\text{Mean volume of destroyed parts} = \text{Destroyed part volume}/\text{Number of destroyed parts} \quad \text{Equation 10}$$

Next, the method of calculating the parameter 13 of FIG. 15, that is, the mean surface area of the destroyed parts, will be explained. The mean surface area of the destroyed parts expresses the mean surface area per destroyed part independent in observation area. Equation 11 shows the method of calculating it:

Mean surface area of destroyed parts=Destroyed part surface area/Number of destroyed parts        Equation 11

The structural parameters from parameter 9 to parameter 13 found by equation 7 to equation 11 show the structural characteristics of the joint destroyed part as a 3D structure and are a group of important indicators in judgement of the state of the joint destroyed part.

Next, the extraction of the JS regions shown in step 8 of FIG. 2 will be explained in the order of the steps.

The JS region is a space between a pair of joint bones. In the same way as the joint destroyed part region, 3D image data of the JS region can be extracted by applying the Expansion and Shrinkage method and Sphere Scanning method to the joint bones to be analyzed for the JS region.

Due to the 3D labeling processing shown in step 4 of FIG. 2, all independent joint parts present in the examined joint region are assigned independent label numbers in the present invention. Due to this, it is possible to designate two 3D structures having any label numbers, in other words, any pair of joint bones, for analysis. Further, similarly, in the present invention, when analyzing the knee joint, it is possible to automatically discriminate and assign label numbers to the joint images to be evaluated, that is, the femur, tibia, patella, and meniscus, from the correspondence of the center of gravity positions of the knee joint. Due to this, it is possible to automatically designate a pair of joint bones of the knee, that is, the femur and tibia, for analysis.

Figure 20:
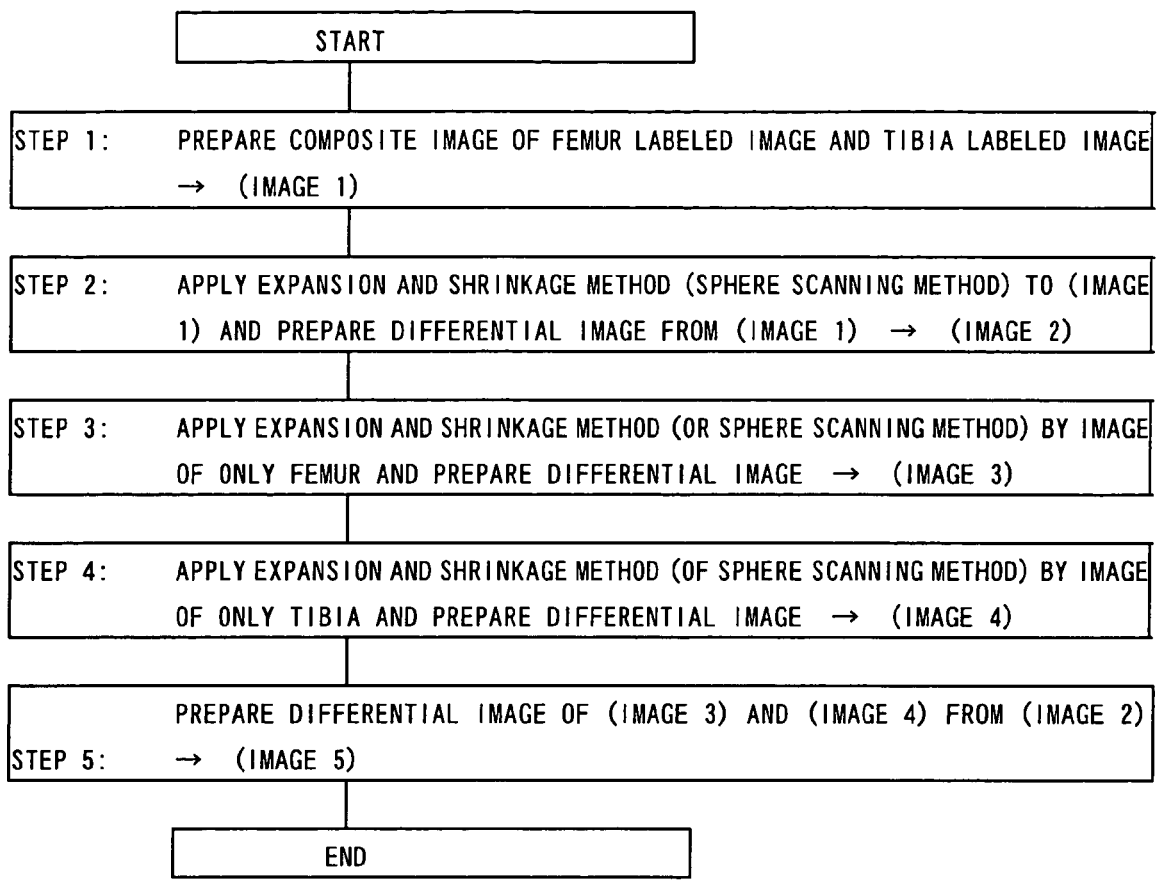
FIG. 20 is a view of the routine of the method of extraction of a JS region.

A flow chart of the method of definition of the JS region is shown in FIG. 20. The specific steps will be explained taking as an example a model of the rat knee joint, that is, the femur and tibia.

Figure 21A:
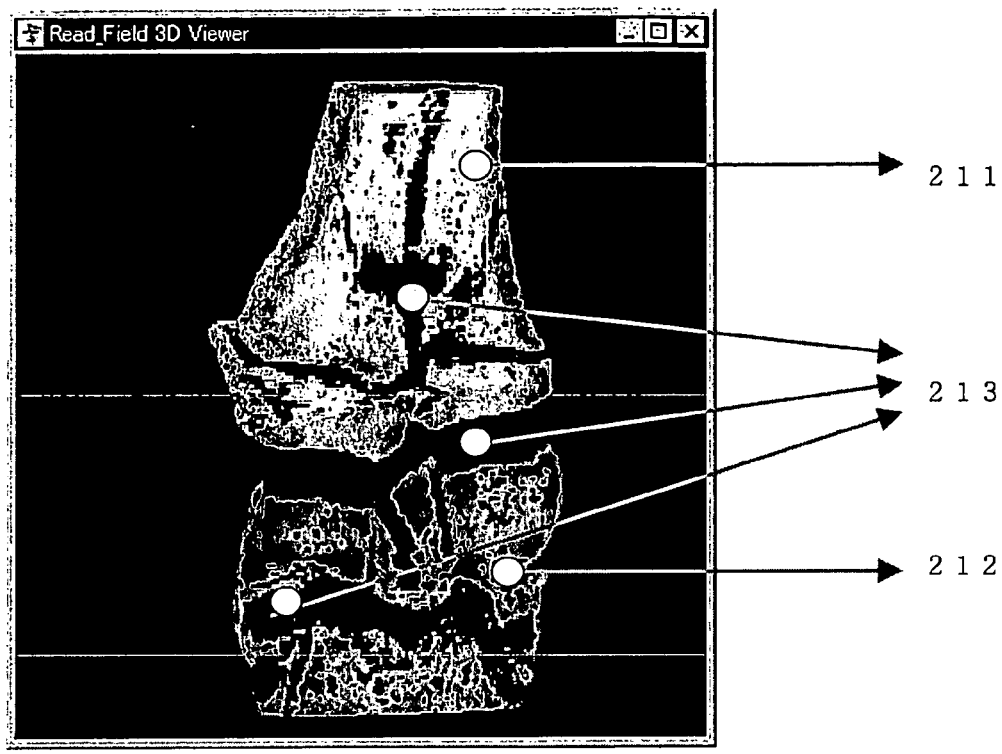
FIG. 21 (FIG. 21A to FIG. 21D) gives explanatory views for defining a JS region.
Figure 21B:
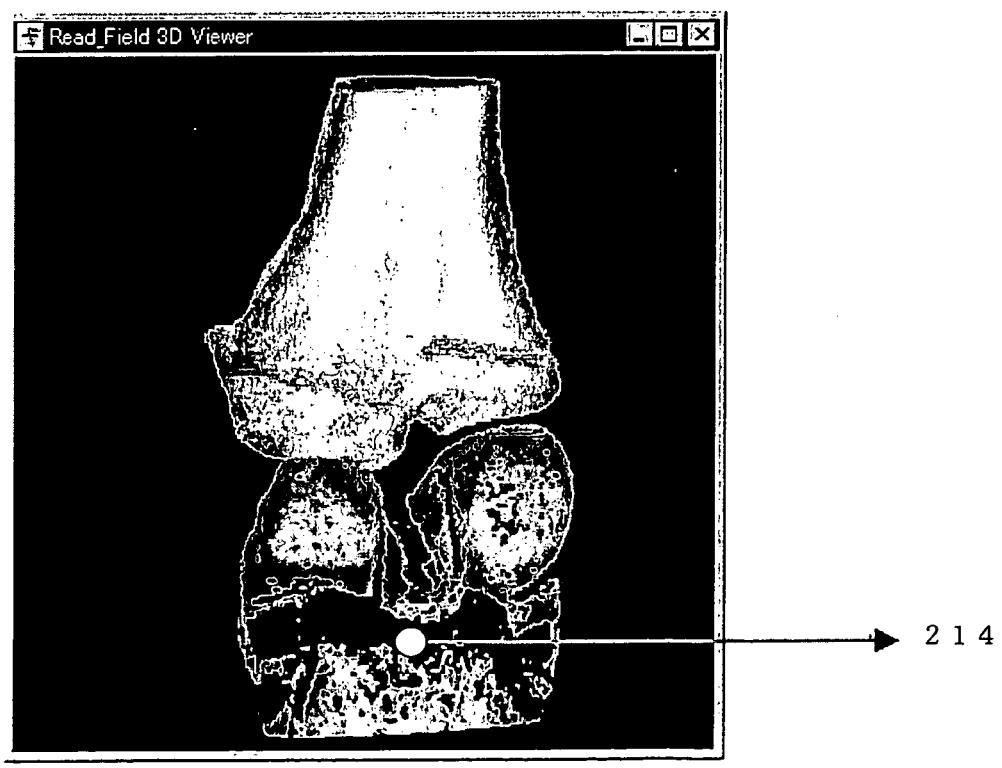
Figure 21C:
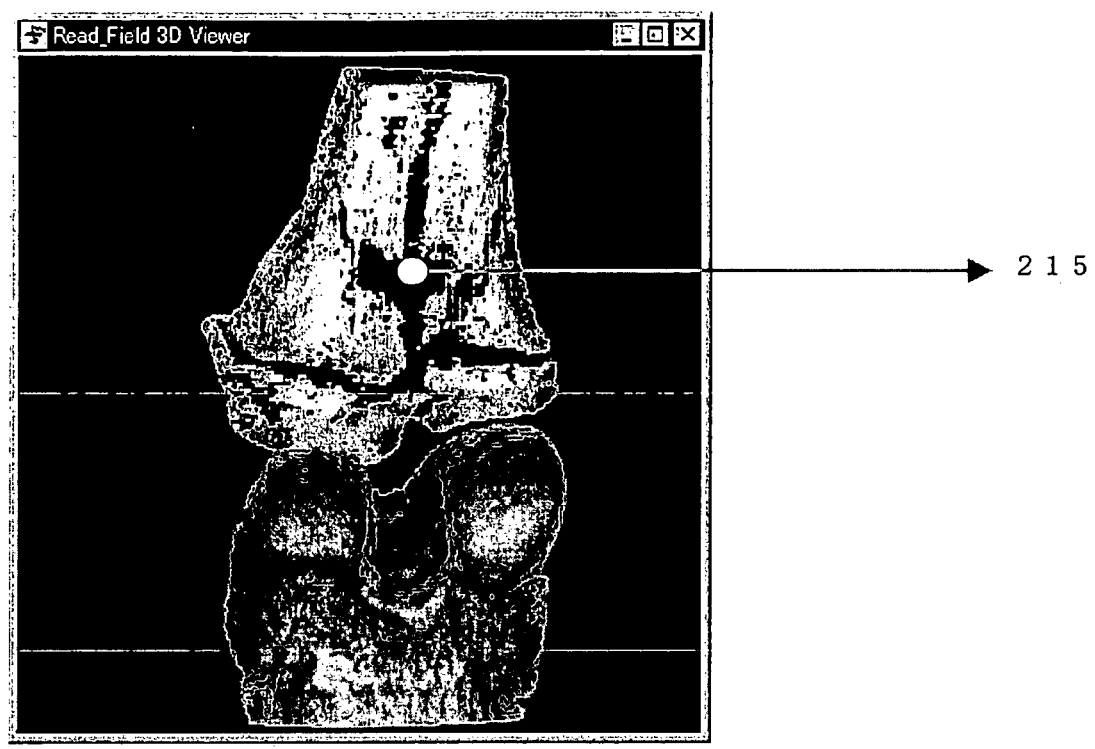
Figure 21D:
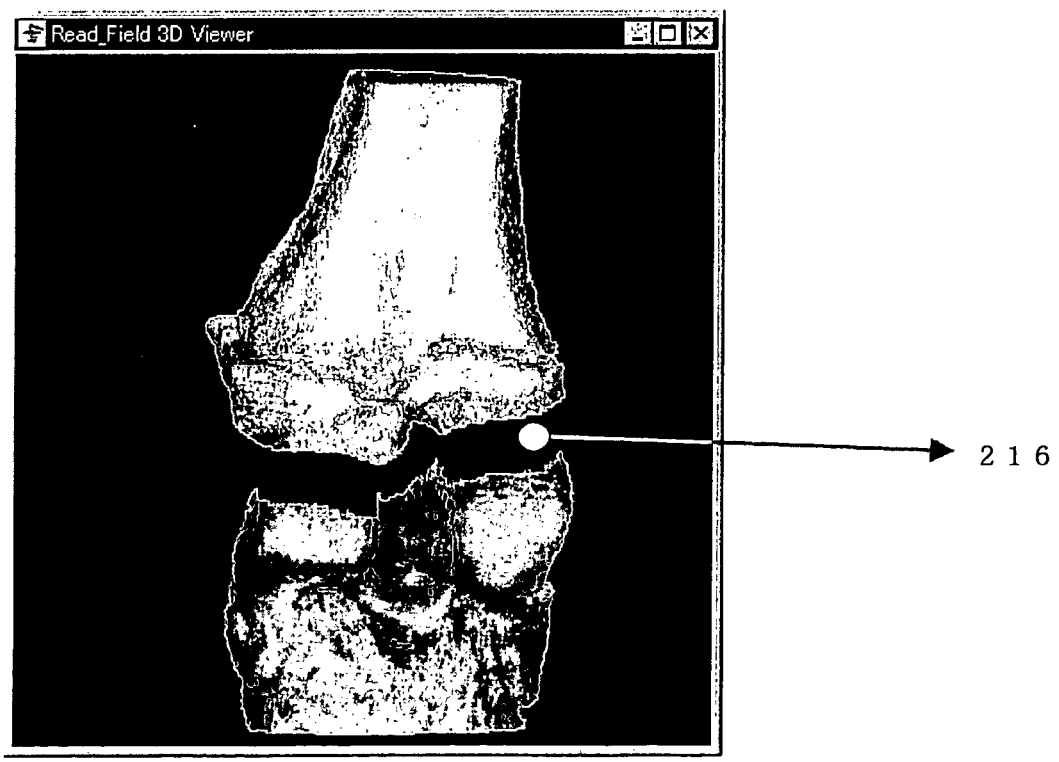
Figures 24, 25A:
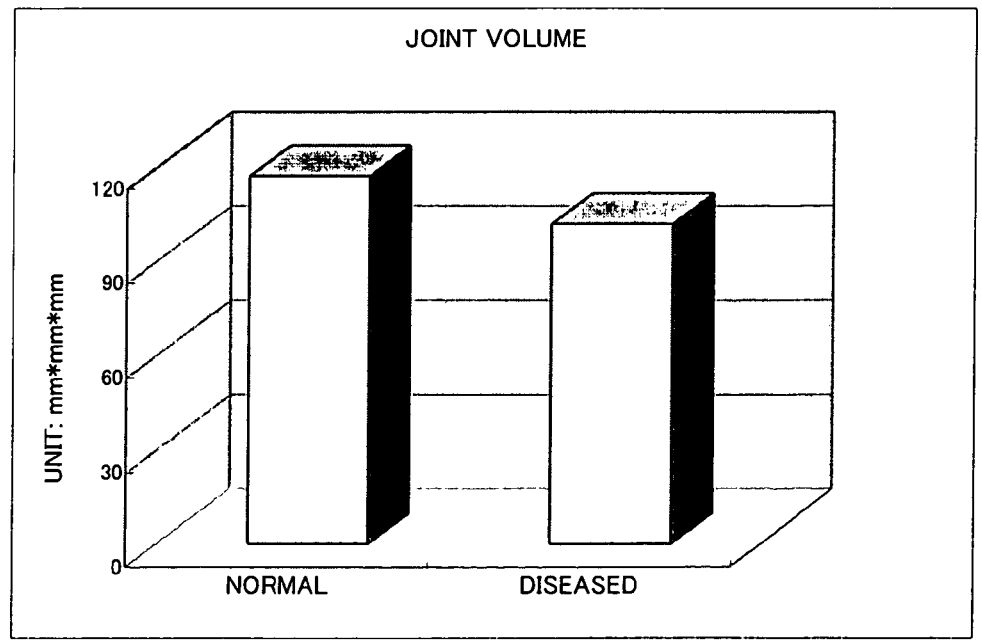
FIG. 24 is an explanatory view of the routine for calculating the Joint Space Minimum Distance.
Figure 25B:
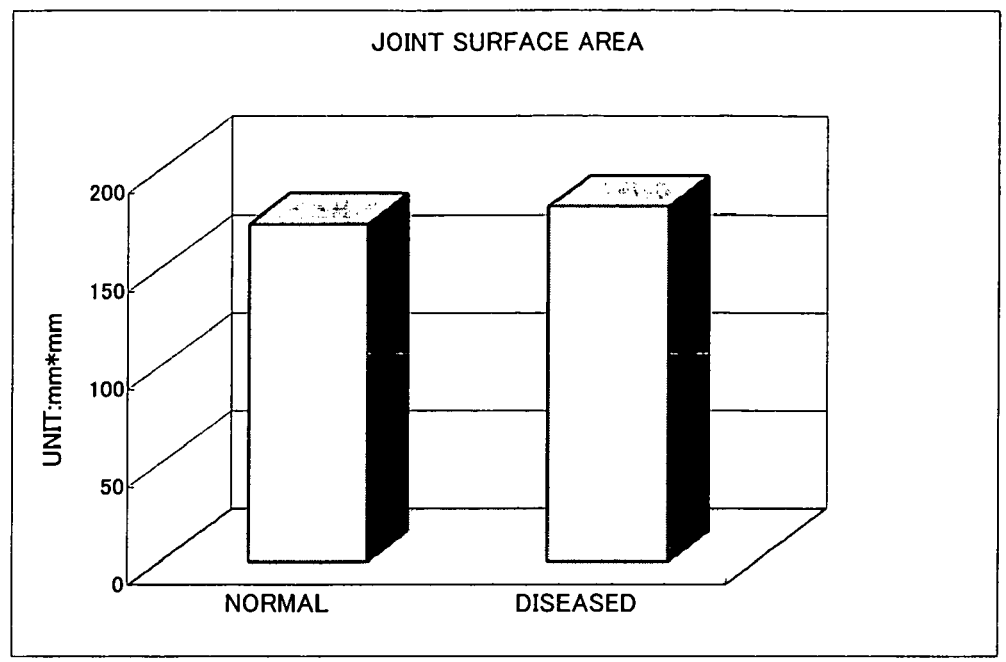
FIG. 25 shows the results of measurement (FIG. 25A to FIG. 25M) of the subchondral bone of a rat femur joint relating to the parameters shown in FIG. 15.
Figure 25C:
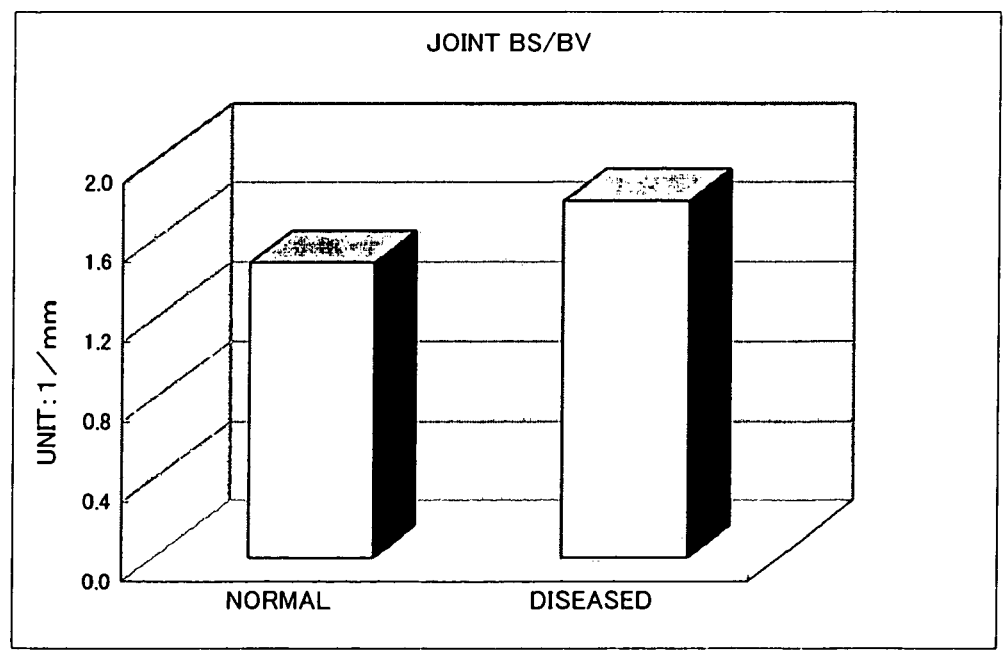
Figure 25D:
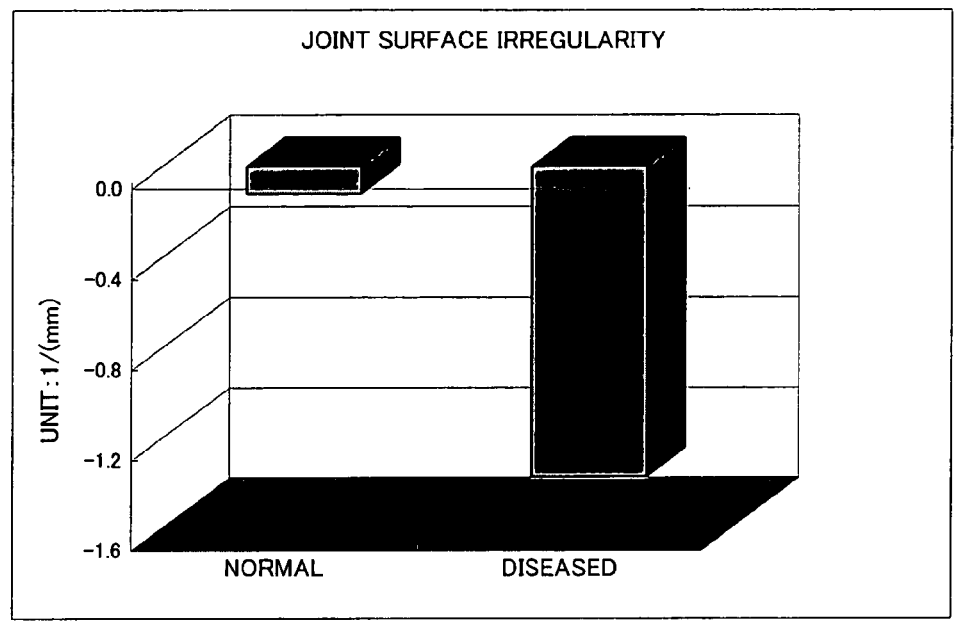
Figure 25E:
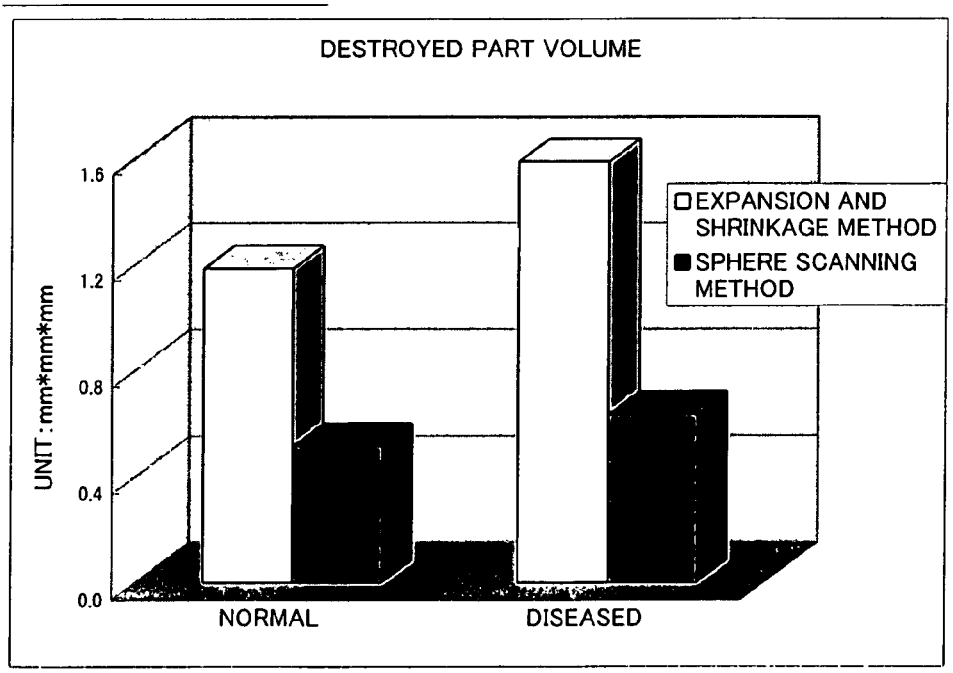
Figure 25F:
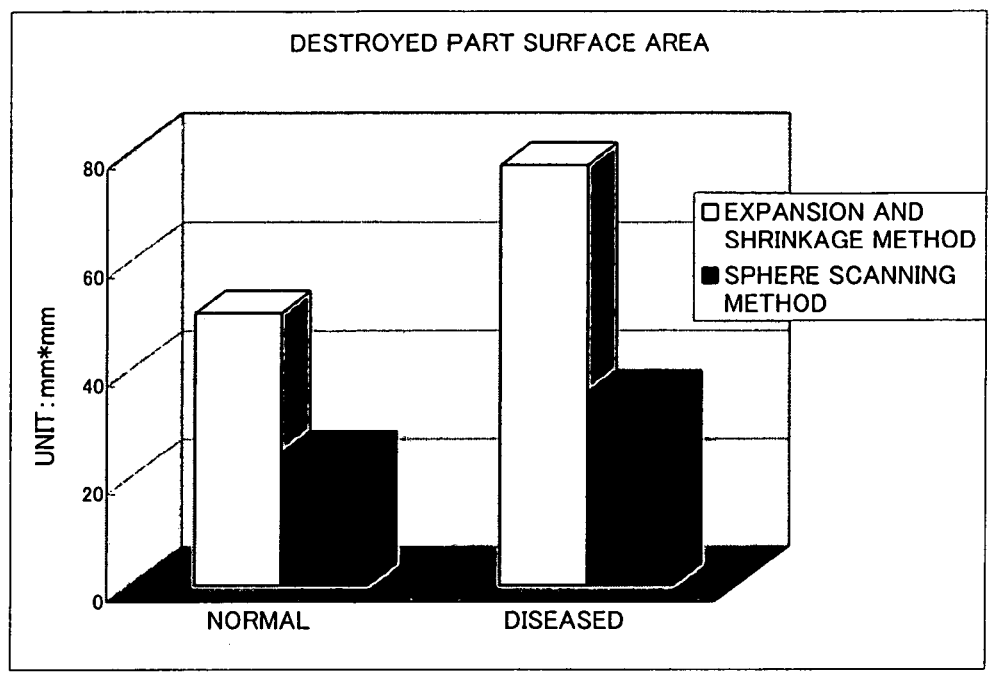
Figure 25G:
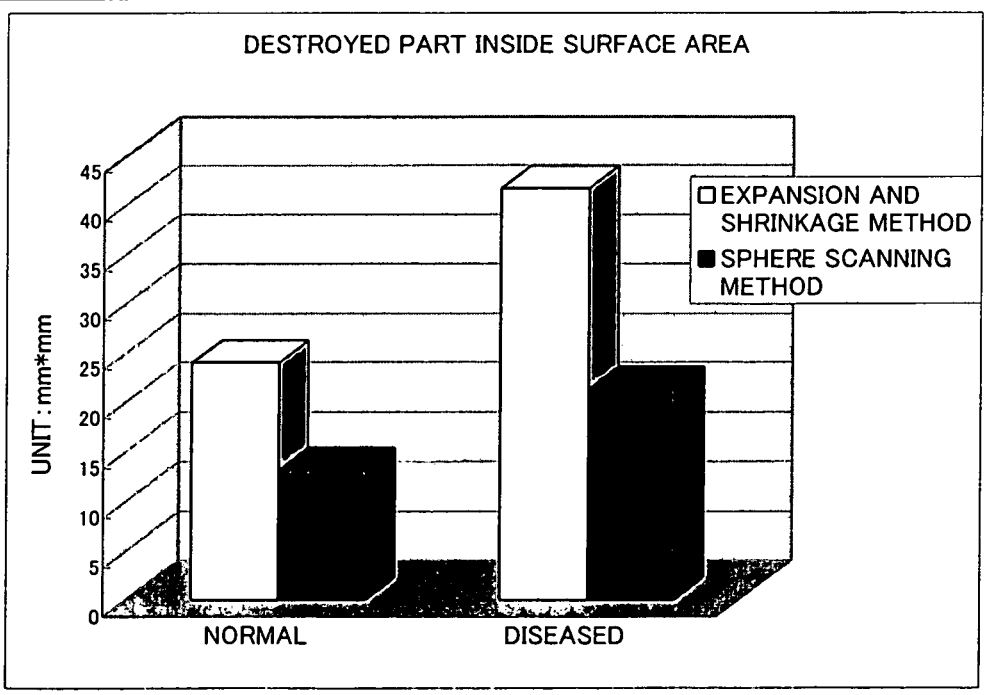
Figure 25H:
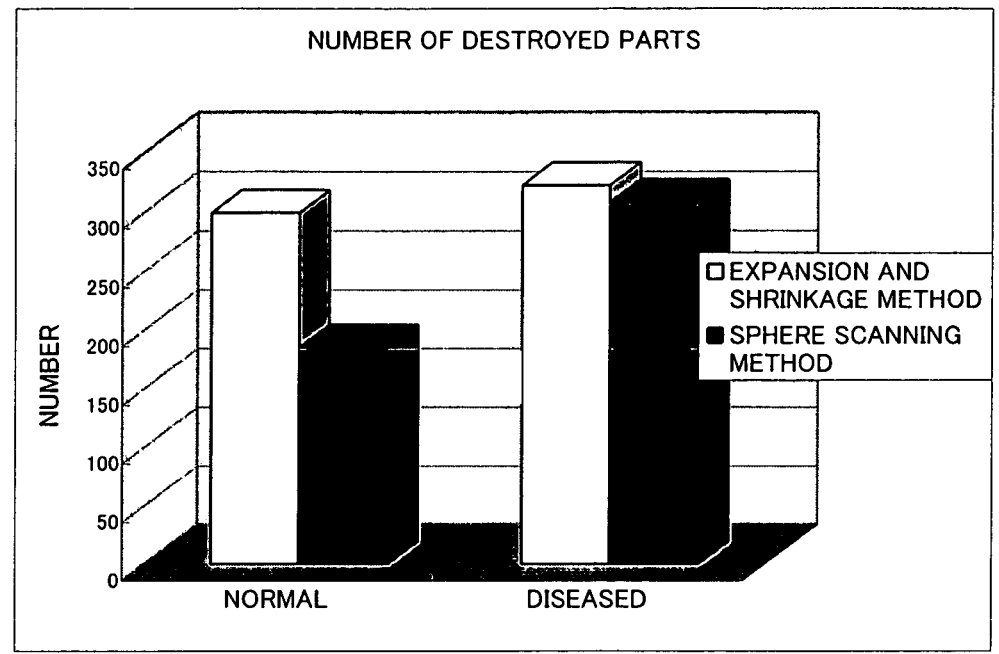
Figure 25I:
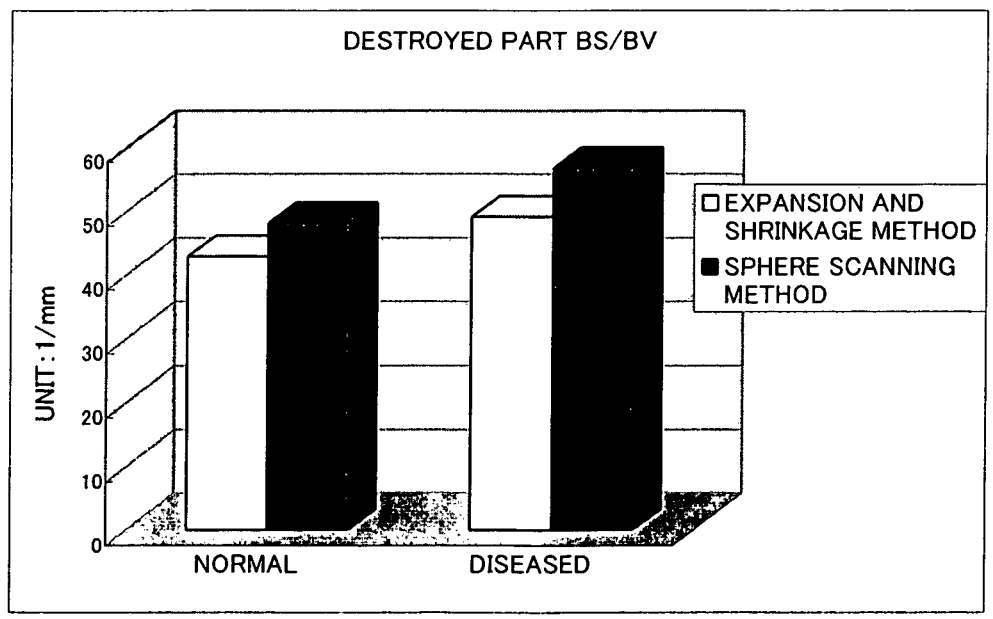
Figure 25J:
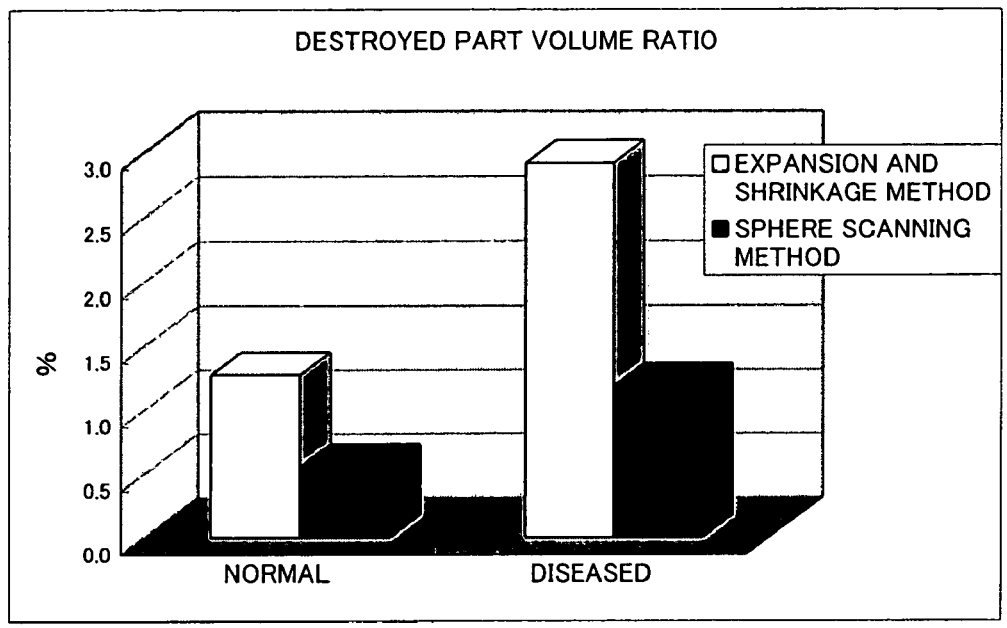
Figure 25K:
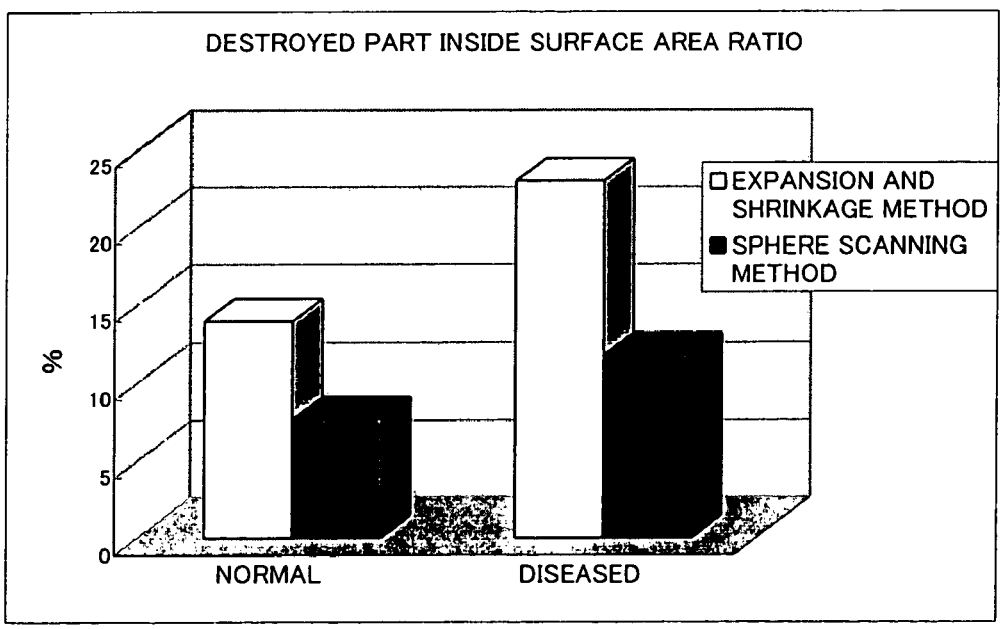
Figure 25L:
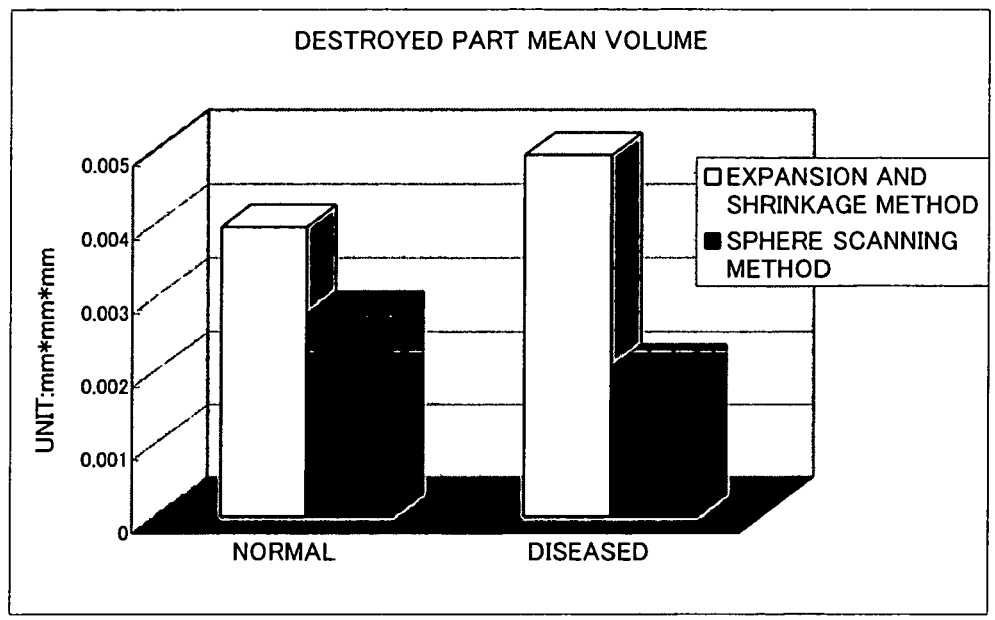
Figure 25M:
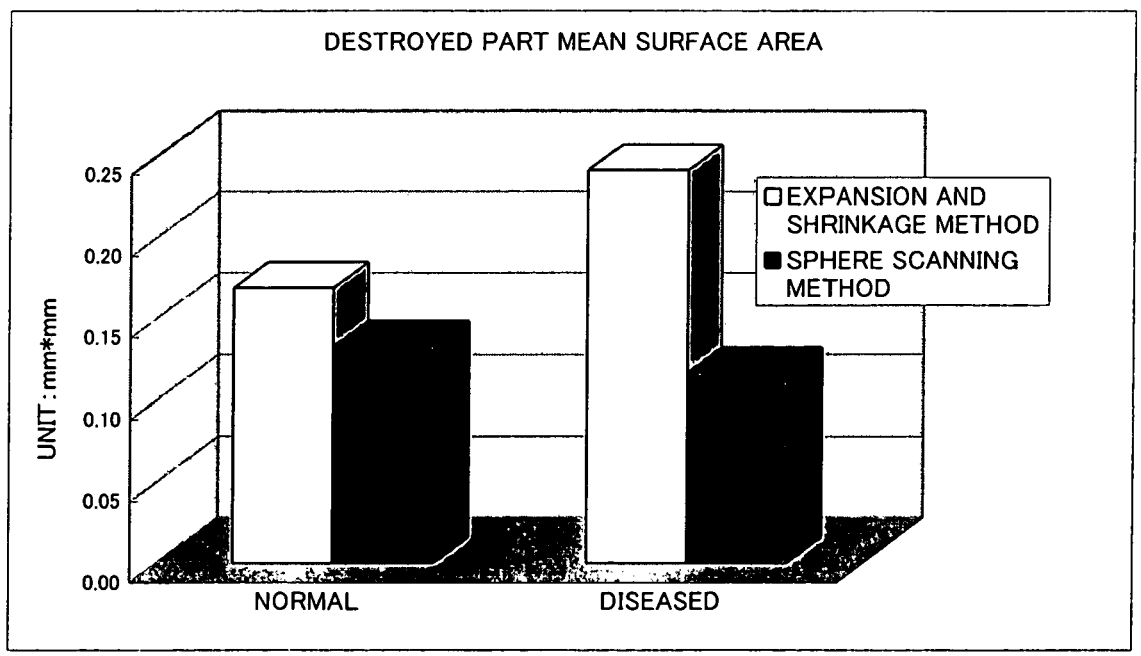

First, at step 1 of FIG. 20, a composite image (image 1) of the two joint bones to be analyzed is created. Next, the Expansion and Shrinkage method (or Sphere Scanning method) is executed in the same way as the joint destroyed part region for the image 1 at step 2 of FIG. 20 to prepare a differential image from the image 1 (image 2: 213 of FIG. 21A). Next, the Expansion and Shrinkage method is executed for the image of only the femur at step 3 of FIG. 20 to extract the joint destroyed part region of the femur and create the image 3 (214 of FIG. 21B). Next, the Expansion and Shrinkage method is executed for the image of only the tibia at step 4 of FIG. 20 to extract the joint destroyed part region of the tibia and create the image 4 (215 of FIG. 21C). Next, if producing the differential images of the image 3 and image 4 from the image 2 at step 5 of FIG. 20, it is possible to define the JS region (image 5: 216 of FIG. 21D). It is possible to extract the JS region even if replacing the Expansion and Shrinkage method shown here with the Sphere Scanning method.

Next, the method of calculation of the JS region parameters of step 9 of FIG. 2 will be explained. The items definable as the JS region parameters are shown in FIG. 22. The handling of the voxel values of the joint part regions, medullary cavity region, JS region, and background region as preconditions are defined as follows:

(e) Femur joint part region→1
(f) Tibia joint part region→2
(g) Medullary cavity region (femur side)→3
(h) Medullary cavity region (tibia side)→4
(i) JS region→5
(j) Background region→0

First, the Joint Space Volume (hereinafter referred to as the JSV) of FIG. 22 will be explained. The JSV is the volume of the JS region. In measuring the JSV, the Advanced Marching Cubes method is applied. Specifically, by defining the cubes sampled by 2×2×2 voxel regions and the boundary surface by pattern matching on the cubes of FIG. 18 for the JS region (i) and other regions (e), (f), (g), (h), and (j) and counting the cube data and boundary surface data, JSV can be measured.

Next, the method of calculation of the Joint Space Minimum Distance (hereinafter referred to as the JSMD) will be explained. The JSMD is the shortest length of the distance between a pair of joint bones, in this example, the shortest distance between the femur distal epiphysis and the tibia proximal epiphysis. A flow chart of the method of calculation of the JSMD is shown in FIG. 23.

Figure 27A:
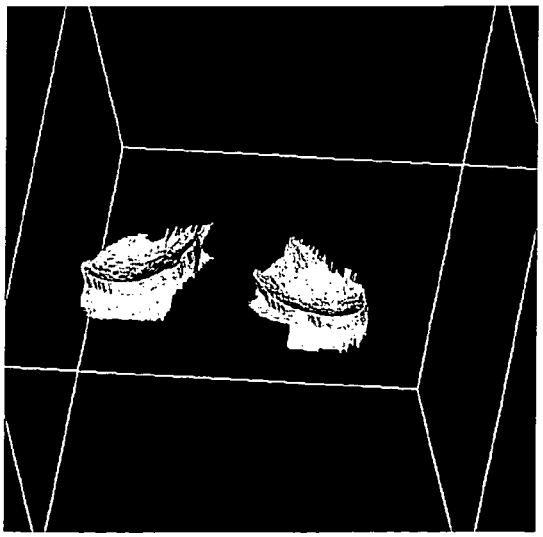
FIG. 27 shows the JS region (FIG. 27A and FIG. 27B) of the knee joint of a guinea pig extracted using the Expansion and Shrinkage method.
Figure 27B:
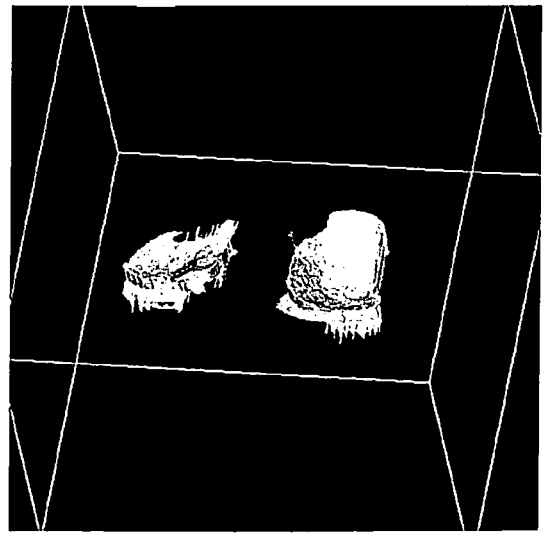

At step 1 of FIG. 23, the voxel coordinates of the femur side where the femur joint part region (e) and the medullary cavity region of femur side (g) have contact with the JS region (i) are listed (list 1). Next, at step 2 of FIG. 23, the voxel coordinates of the tibia side where the tibia joint part region (f) and the medullary cavity region of tibia side (h) have contact with the JS region (i), are listed (list 2). In the above processing, as shown in FIG. 27, the voxel list (241) of the femur side and the voxel list (242) of the tibia side contacting the JS region could be extracted. At step 3 of FIG. 23, the distance data from the voxel coordinate list (241) of the femur side to the voxel coordinate list (242) of the tibia side is found and the shortest distance is made the JSMD.

Next, an example of analysis will be shown and its meaning and usefulness explained for the 3D structural parameters able to be analyzed in the present invention.

FIG. 25 shows the results of analysis of the parameters relating to the destroyed part shown in FIG. 15 for the femur joint part of a normal rat (hereinafter referred to as "normal") and the femur joint part of a rat having joint destruction (hereinafter referred to as "diseased").

It was possible to detect an increase in the destroyed part between the normal and diseased states both in the parameters directly measuring the joint part (in this example, the sub-chondral bone) (FIG. 25A to FIG. 25D) and in the parameters measuring the extracted destroyed part (FIG. 25E to FIG. 25M).

Figure 26:
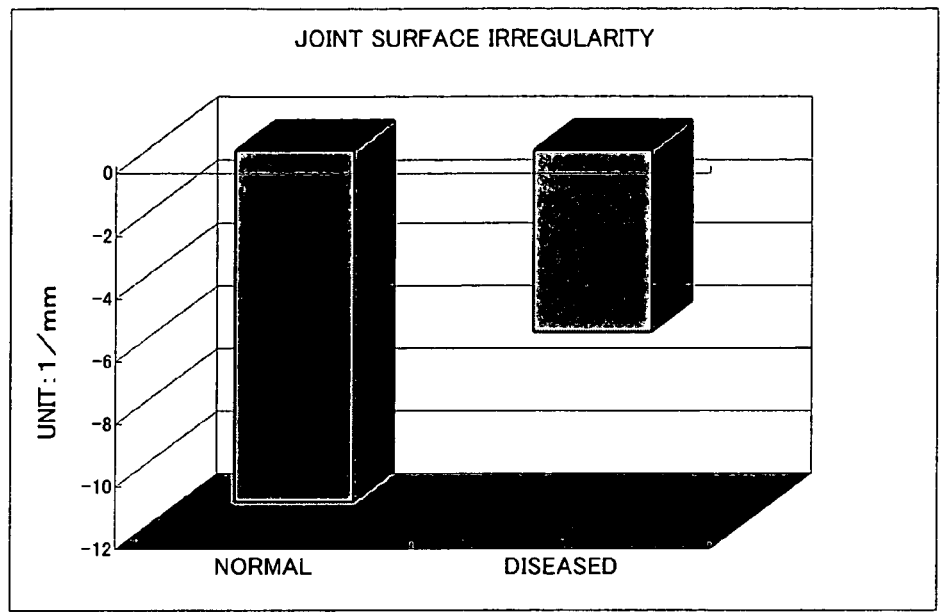
FIG. 26 shows the results of measurement of surface irregularity in the case of not performing the processing for filling the joint inside structure.

The increase in the joint BS/BV in the diseased state (FIG. 25C) means an increase in the complexity of the surface structure, while a decrease in the irregularity of the joint surface (FIG. 25D) means an increase in the surface recessed structures. Changes in any parameter mean an increase in the destruction of the joint in the diseased state. In particular, for irregularities of the joint surface, by performing the processing for filling the inside of the joint performed in the present patent, changes in shape of the joint surface can be specifically extracted for the first time. The results of measurement of the irregularity of the joint surface without performing processing for filling the inside of the joint are shown in FIG. 26 as a comparative example. Unlike the case of performing the filling processing (FIG. 25D), the normal state gives lower values than the diseased state and the normal state gives more surface recessed structures than the diseased state. This is because in the normal state compared with the diseased state, there are more structures inside the joint, that is, trabeculars, and more complicated structures are formed. From these facts, according to the present invention, it can be said that the sensitivity of detection of structural changes of the joint structure is strikingly improved.

Further, in the results of measurement of the destroyed part extracted by the two types of algorithms (Expansion and Shrinkage method and Sphere Scanning method), all parameters increase in the diseased state compared with the normal state. According to the present invention, it was possible to detect that the destruction of the joint increases in the diseased state.

Further, compared with the Expansion and Shrinkage method, the Sphere Scanning method enables lower values to be obtained (FIG. 25E to FIG. 25M). This is due to the characteristics of the two types of extraction methods. Explained more specifically, the Expansion and Shrinkage method accurately extracts even fine changes in the surface structure, while the Sphere Scanning method tolerates gentle irregularity of the surface. By selectively using the two types of algorithms (Expansion and Shrinkage method and Sphere Scanning method) in accordance with the targeted evaluation object, it is possible to more accurately detect changes in the detailed surface structure.

Next, the effects of analysis of the JS region in the knee joint of a normal guinea pig (hereinafter "normal") and the knee joint of a guinea pig having joint destruction (hereinafter "diseased") will be explained.

FIG. 27 shows the JS region extracted by the Expansion and Shrinkage method for the normal and diseased states. In both examples, it was confirmed that the JS region is accurately extracted by itself. According to the present invention, it is shown that three-dimensional visualization and extraction of the JS region, which have been difficult up until now, are possible. The JS region can be similarly extracted even by the Sphere Scanning method.

Figure 28:
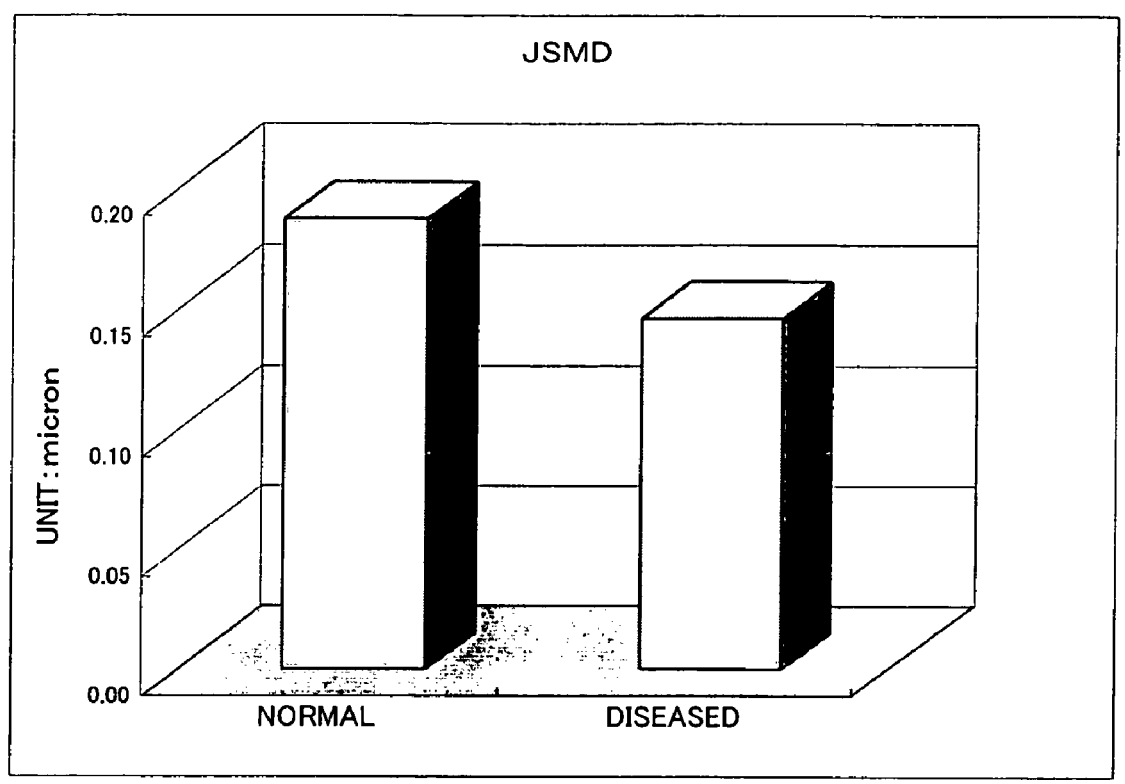
FIG. 28 shows the results of measurement of the JSMD of the knee joint JS region of a guinea pig shown in FIG. 27.

Next, FIG. 28 shows the results of measurement of the JSMD for normal and diseased JS regions shown in FIG. 27. In the diseased state, a reduction in the JSMD was observed. Compared with the normal state, it was observed that destruction or disappearance of the joint cartilage occurred.

From the above, according to the present invention, it has become possible to visually recognize three-dimensionally the JS region and to analyze the 3D structural parameters objectively, quantitatively, with a good repeatability.

EFFECTS OF THE INVENTION

In the present invention, it has become possible to extract the structure of the joint surface with good sensitivity by processing for filling the joint inside structure and to extract the recessed structure region from the joint, that is, the destroyed part, at a high speed, simply, with a good repeatability by the development of two types of image processing methods. Further, the image data of the joint surface and destroyed part obtained can provide structural indicators relating to joint destruction by 3D structural analysis. Further, by analyzing the pair of joint bones forming a joint, it has become possible to analyze the 3D structure of a JS region at a high speed with a good repeatability.

Further, it becomes possible to extract the joint surface and destroyed part using the same algorithm, so it is possible to objectively and quantitatively evaluate the structural characteristics of the joint surface and destroyed part with good repeatability without the subjective judgement of the observer when analyzing several joints, that is, even in analysis of the change over time of the same patient or judgement of the therapeutic effects of administration and non-administration of drugs.

Further, it is possible to display the joint part and joint destroyed part defined in the present invention using a visualization tool and becomes possible to visually provide to an observer 3D spatial-like information for the joint surface structure and the joint destroyed part of the joint. Further, the analysis of the 3D joint structure according to the present invention can be applied to not only the knee joint, but also other joint.

Further, the present invention can be expected to be allow all of the diagnostic image information obtained from a μX-ray CT apparatus or other clinical CT apparatus, PQCT photographic apparatus, MRI, etc. to be applied to measurement of the 3D structure of a joint.

The invention claimed is:

1. An image processing method comprising steps of:
    extracting, using a processor, a medullary cavity region comprising a hollow region inside a joint from a digitalized image of a cross section of examined joint bones only, using an Expansion and Shrinkage method, and further using the processor;
    filling the medullary cavity region by figuring out a sum of the extracted medullary cavity region and the digitalized image of the cross-section of the examined joint bones;
    extracting a surface structure of the joint bones, whereby generating a digitalized image of the cross-section of the examined joint bones;
    stacking a plurality of the digitalized images of a plurality of the digitalized images of a plurality of the cross sections of the examined joint bones so as to obtain a 3D image;
    performing 3D labeling for the 3D image so as to define a 3D joint image to be evaluated; and
    judging, identifying, and extracting a joint image to be evaluated from correspondence of centers of gravity positions of each of the joint bones.

2. An image processing method for judging, identifying, and extracting a joint image of a femur, tibia, patella, and/or meniscus to be evaluated from a relative relationship of center of gravity positions of joint bones using a 3D label image of joint bones prepared by the image processing method of claim 1.

3. An image processing method having the step of extracting a 3D image of a joint destroyed part using the 3D image expansion method and 3D image shrinkage method for a 3D bone image of a joint defined by the image processing method of claim 1.

4. An image processing method having the step of extracting a 3D image of a joint destroyed part using the 3D Sphere Scanning method for a 3D bone image of a joint defined by the image processing method of claim 1.

5. An image processing method having the step of extracting a 3D image of a joint destroyed part using the 3D image expansion method and 3D image shrinkage method for a 3D bone image of a joint defined by the image processing method of claim 2.

6. An image processing method having the step of extracting a 3D image of a joint destroyed part using the 3D Sphere Scanning method for a 3D bone image of a joint defined by the image processing method of claim 2.

7. A joint structure evaluation method comprising measuring Joint BS/BV and/or Joint Surface Irregularity for a 3D image of a joint bone produced by the image processing method of one of claims 1 and 2.

8. A joint structure evaluation method comprising measuring structural parameters of volume (BV), surface area (BS), BS/BV, the number, average volume (volume/number), and/or mean surface area (surface area/number) for a 3D structure produced by the image processing method of any one of claims 1, 2 and 3 to 6.

9. An image processing method having the step of extracting a 3D image of joint space using the 3D image expansion method and 3D image shrinkage method for any two analysis objects in a 3D bone image of a joint defined by the image processing method of claim 1.

10. An image processing method having the step of extracting a 3D image of joint space using the 3D Sphere Scanning method for any two analysis objects in a 3D bone image of a joint defined by the image processing method of claim 1.

11. An image processing method having the step of extracting a 3D image of joint space using the 3D image expansion method and 3D image shrinkage method for any two analysis objects in a 3D bone image of a joint defined by the image processing method of claim 2.

12. An image processing method having the step of extracting a 3D image of joint space using the 3D Sphere Scanning method for any two analysis objects in a 3D bone image of a joint defined by the image processing method of claim 2.

13. A joint structure evaluation method measuring structural parameters of the Joint Space Volume (JSV) and Joint Space Minimum Distance (JSMD) for a 3D structure produced by the image processing methods of any one of claims 9 to 12.

14. An evaluation method for evaluating the structure of a joint in an animal model of a joint related ailment using the method of claim 1.

15. An evaluation method for evaluating the structure of a joint of a patient of a joint related ailment using the method of claim 1.

16. A diagnosis method for diagnosing joint destruction of a patient of a joint related ailment using the method of claim 1.

* * * * *